US 7,375,814 B2
May 20, 2008

(12) United States Patent
Reichardt et al.

(54) NATURAL GAS LEAK MAPPER

(75) Inventors: Thomas A. Reichardt, Livermore, CA (US); Amy Khai Luong, Dublin, CA (US); Thomas J. Kulp, Livermore, CA (US); Sanjay Devdas, Albany, CA (US)

(73) Assignee: Sandia Corporation, Livermore, CA (US)

( * ) Notice: Subject to any disclaimer, the term of this patent is extended or adjusted under 35 U.S.C. 154(b) by 216 days.

(21) Appl. No.: 11/078,527

(22) Filed: Mar. 11, 2005

(65) Prior Publication Data
US 2006/0203248 A1    Sep. 14, 2006

(51) Int. Cl.
G01N 21/01    (2006.01)
G01N 21/00    (2006.01)
(52) U.S. Cl. .................................. 356/437; 250/330
(58) Field of Classification Search ................ 356/437; 372/22; 250/334, 338.5
See application file for complete search history.

(56) References Cited

U.S. PATENT DOCUMENTS

| | | | | |
|---|---|---|---|---|
| 3,317,730 A | * | 5/1967 | Hilsum ...................... | 250/338.5 |
| 3,609,389 A | | 9/1971 | Bjorkholm ................. | 307/88.3 |
| 3,628,186 A | | 12/1971 | Rumson et al. .......... | 331/107 R |
| 3,948,345 A | | 4/1976 | Rosencwaig ............... | 181/0.5 |
| 4,058,725 A | | 11/1977 | Aine .......................... | 250/343 |
| 4,457,162 A | | 7/1984 | Rush et al. ................. | 73/24.01 |
| 4,489,239 A | * | 12/1984 | Grant et al. ............ | 250/339.03 |
| 4,490,613 A | | 12/1984 | Brame ........................ | 250/341 |
| 4,496,839 A | * | 1/1985 | Bernstein et al. ........ | 250/341.6 |
| 4,555,627 A | * | 11/1985 | McRae, Jr. ................. | 250/334 |
| 4,622,845 A | | 11/1986 | Ryan et al. ..................... | 73/24 |
| 4,745,276 A | * | 5/1988 | Broicher et al. ............ | 250/253 |
| 4,772,789 A | | 9/1988 | Maram et al. .............. | 250/330 |

(Continued)

FOREIGN PATENT DOCUMENTS

| | | |
|---|---|---|
| EP | 0 857 997 B1 | 10/2001 |
| WO | WO 98/01927 | 1/1998 |
| WO | WO 02/27297 A1 | 4/2002 |

OTHER PUBLICATIONS

M. J. T. Milton and P. T. Woods, "Pulse averaging methods for a laser remote monitoring system using atmospheric backscatter," Applied Optics, 26, No. 13, 2598 (1987).

(Continued)

Primary Examiner—L. G. Lauchman
Assistant Examiner—Jarreas C Underwood
(74) Attorney, Agent, or Firm—Steven R. Vosen

(57) ABSTRACT

A system is described that is suitable for use in determining the location of leaks of gases having a background concentration. The system is a point-wise backscatter absorption gas measurement system that measures absorption and distance to each point of an image. The absorption measurement provides an indication of the total amount of a gas of interest, and the distance provides an estimate of the background concentration of gas. The distance is measured from the time-of-flight of laser pulse that is generated along with the absorption measurement light. The measurements are formated into an image of the presence of gas in excess of the background. Alternatively, an image of the scene is superimosed on the image of the gas to aid in locating leaks. By further modeling excess gas as a plume having a known concentration profile, the present system provides an estimate of the maximum concentration of the gas of interest.

6 Claims, 8 Drawing Sheets

U.S. PATENT DOCUMENTS

| | | | | |
|---|---|---|---|---|
| 5,001,346 | A | * | 3/1991 | Barkhoudarian ............ 250/330 |
| 5,097,477 | A | | 3/1992 | Scheps ........................ 372/94 |
| 5,117,126 | A | | 5/1992 | Geiger ....................... 359/330 |
| 5,159,411 | A | | 10/1992 | Hammerich et al. ........ 356/432 |
| 5,202,560 | A | | 4/1993 | Koch et al. ................. 356/435 |
| 5,294,796 | A | * | 3/1994 | Fee .......................... 250/338.5 |
| 5,298,751 | A | * | 3/1994 | Fee et al. ................. 250/338.5 |
| 5,373,160 | A | * | 12/1994 | Taylor ..................... 250/338.5 |
| 5,430,293 | A | | 7/1995 | Sato et al. .................. 250/330 |
| 5,434,700 | A | | 7/1995 | Yoo ........................... 359/332 |
| 5,523,569 | A | * | 6/1996 | Hornfeld et al. ............ 250/330 |
| 5,656,813 | A | | 8/1997 | Moore et al. ............... 250/330 |
| 5,815,277 | A | | 9/1998 | Zare et al. .................. 356/437 |
| 5,864,644 | A | | 1/1999 | DiGiovanni et al. | |
| 5,903,358 | A | | 5/1999 | Zare et al. .................. 356/437 |
| 6,157,033 | A | | 12/2000 | Chudnovsky | |
| 6,202,470 | B1 | | 3/2001 | Chou ........................ 73/24.02 |
| 6,229,828 | B1 | | 5/2001 | Sanders et al. ............... 372/22 |
| H1965 | H | | 6/2001 | Burns et al. .................. 372/22 |
| 6,304,237 | B1 | | 10/2001 | Karakawa ..................... 345/84 |
| 6,324,326 | B1 | | 11/2001 | Dejneka et al. ............. 385/123 |
| 6,344,647 | B1 | | 2/2002 | Jourdain et al. ....... 250/339.07 |
| 6,359,914 | B1 | | 3/2002 | Powers et al. ................ 372/25 |
| 6,455,854 | B1 | | 9/2002 | Richman .................... 250/343 |
| 6,618,148 | B1 | | 9/2003 | Pilgrim et al. .............. 356/432 |
| 6,664,533 | B1 | * | 12/2003 | van der Laan et al. .. 250/222.2 |
| 6,690,472 | B2 | * | 2/2004 | Kulp et al. ................. 356/437 |
| 6,750,453 | B1 | | 6/2004 | Nelson et al. ........... 250/338.5 |
| 6,750,467 | B2 | * | 6/2004 | Tulip .......................... 250/573 |
| 6,751,010 | B1 | | 6/2004 | Richter ....................... 359/330 |
| 6,756,592 | B1 | | 6/2004 | Smith et al. ............. 250/338.5 |
| 6,757,096 | B2 | | 6/2004 | Schiller ....................... 359/330 |
| 6,813,429 | B2 | | 11/2004 | Price et al. ................. 385/125 |
| 6,943,884 | B2 | * | 9/2005 | Rice ........................... 356/437 |
| 6,995,846 | B2 | * | 2/2006 | Kalayeh et al. ............. 356/437 |
| 7,151,787 | B2 | * | 12/2006 | Kulp et al. .................... 372/70 |
| 2002/0017617 | A1 | | 2/2002 | Schuth et al. ............ 250/492.1 |
| 2003/0081192 | A1 | | 5/2003 | Nishi .......................... 355/69 |
| 2003/0188581 | A1 | | 10/2003 | Roudil et al. ................. 73/601 |
| 2004/0006276 | A1 | | 1/2004 | Demos et al. .............. 600/476 |
| 2004/0036957 | A1 | | 2/2004 | Galvanauskas et al. .. 359/341.3 |
| 2004/0095579 | A1 | | 5/2004 | Bisson et al. ............... 356/432 |
| 2004/0263852 | A1 | * | 12/2004 | Degtiarev et al. .......... 356/437 |

OTHER PUBLICATIONS

N. Menyuk, D. K. Killinger, and C. R. Menyuk, "Limitations of signal averaging due to temporal correlation in laser remote-sensing measurements," Applied Optics, 21, No. 18, 3377 (1982).

T. G. McRae and T. J. Kulp, "Backscatter absorption gas imaging: a new technique for gas visualization," Applied Optics, 32, No. 21, 4037 (1993).

T. J. Kulp, P. Powers, R. Kennedy, and U. Goers, "Development of a pulsed backscatter-absorption gas-imaging system and its application to the visualization of natural gas leaks," Applied Optics, 37, No. 18, 3912 (1998).

Optics Letters, vol. 21, No. 17; Bosenberg, et al., "*93% pump depletion, 3.5-W continuous-wave, singly resonant optical parametric oscillator,*" pp. 1336-1338, Sep. 1, 1996.

Springer-Verlag; Applied Physics B, Lasers and Optics; D.G. Lancaster, et al.; "*Portable fiber-coupled diode-laser-based sensor for multiple trace gas detection,*" pp. 459-465; Rice University, Houston, TX., Jun. 24, 1999.

CLEO 2001 Conference; Goers, et al., "*Development of a compact gas imaging sensor employing a cw fiber-amp-pumped PPLN OPO,*" Baltimore, MD, May 6-11, 2001.

J.H. Price et al., " A tuneable, femtosecond pulse source operating in the range 1.06-1.33 microns based on an Yb doped holey fiber amplifier", Apr. 11, 2001, Optoelectronics Research Centre, University of Southhampton.

Thomas Graf et al., "Synchronously pumped optical parametric oscillation in periodically poled lithium niobate with 1-W average output power", *Applied Optics*, pp. 3324-3328, vol. 38, No. 15, May 20, 1999.

Gregory David Miller, "Periodically Poled Lithium Niobate: Modeling, Fabrication, and Nonlinear-Optical Performance", Ph.D. Dissertation, Stanford University, Jul. 1998.

L. Goldberg, J. Koplow, D. G. Lancaster, R. F. Curl, and F. K. Tittel, "Mid-infrared difference-frequency generation source pumped by a 1.1-1.5-μm dual-wavelength fiber amplifier for trace-gas detection", *Optics Letters*, vol. 23, No. 19, Oct. 1, 1998, pp. 1517-1519.

D. G. Lancaster, D. Richter, R. F. Curl, F. K. Tittel, L. Goldberg, and J. Koplow, "High-power continuous-wave mid-infrared radiation generated by difference frequency mixing of diode-laser-seeded fiber amplifiers and its application to dual-beam spectroscopy", *Optics Letters*, vol. 24, No. 23, Dec. 1, 1999, pp. 1744-1746.

H. Dahnke, D. Kleine, p. Hering, and M. Mürtz, "Real-time monitoring of ethane in human breath using mid-infrared cavity leak-out spectroscopy", *Appl. Phys. B 72*, May 9, 2001, pp. 971-975.

Naoya Matsuoka, Shigeru Yamaguchi, Kenzo Nanri, Tomoo Fujioka, Dirk Richter and Frank K. Tittel, "Yb Fiber Laser Pumped Mid-IR Source Based on Difference Frequency Generation and Its Application to Ammonia Detection", *Jpn. J. Appl. Phys.*, vol. 40, Part 1, No. 2A, Feb. 2001, pp. 625-628.

Uta-Barbara Goers, Karla Armstrong, Ricky Sommers, Thomas J. Kulp, Dahv A.V. Kliner, Sal Birtola, Lew Goldberg, Jeffrey P. Koplow, and T.G. McRae, "Development of a compact gas imaging sensor employing a cw fiber-amp-pumped PPLN OPO", Presentation at CLEO, Apr. 2001.

Scott E. Bisson, Karla A. Armstrong, Thomas J. Kulp, and Matthew Hartings, "Broadly tunable, mode-hop-tuned cw optical parametric oscillator based on periodically poled lithium niobate", *Applied Optics*, vol. 40, No. 33, Nov. 20, 2001, pp. 6049-6055.

CDRL Report No. A009, "Commercialization of Technologies to Lower Defense Costs, Draft Laser-Based Sensors for VOCs, Technology Assessment", 19 pages, Mar. 22, 2002.

"Construction of CW Optical Parametric Oscillators", http//www.nat.vu.nl/vakgroepen/atom/english/research/appspec/opos.html, Aug. 15, 2002.

SERDP Fact Sheet, "Sensors for VOC/NOx and Metal Particulate Emissions Monitoring", Mar. 25, 1999.

* cited by examiner

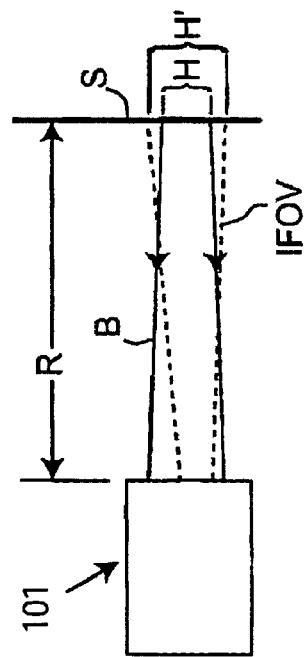
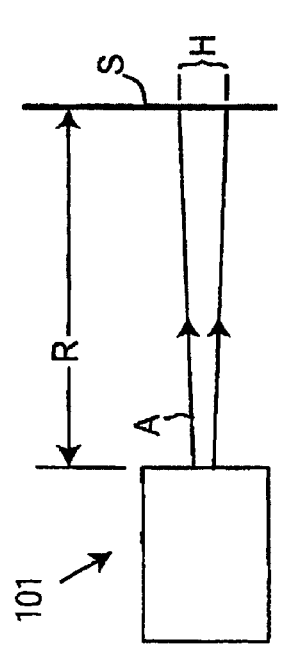
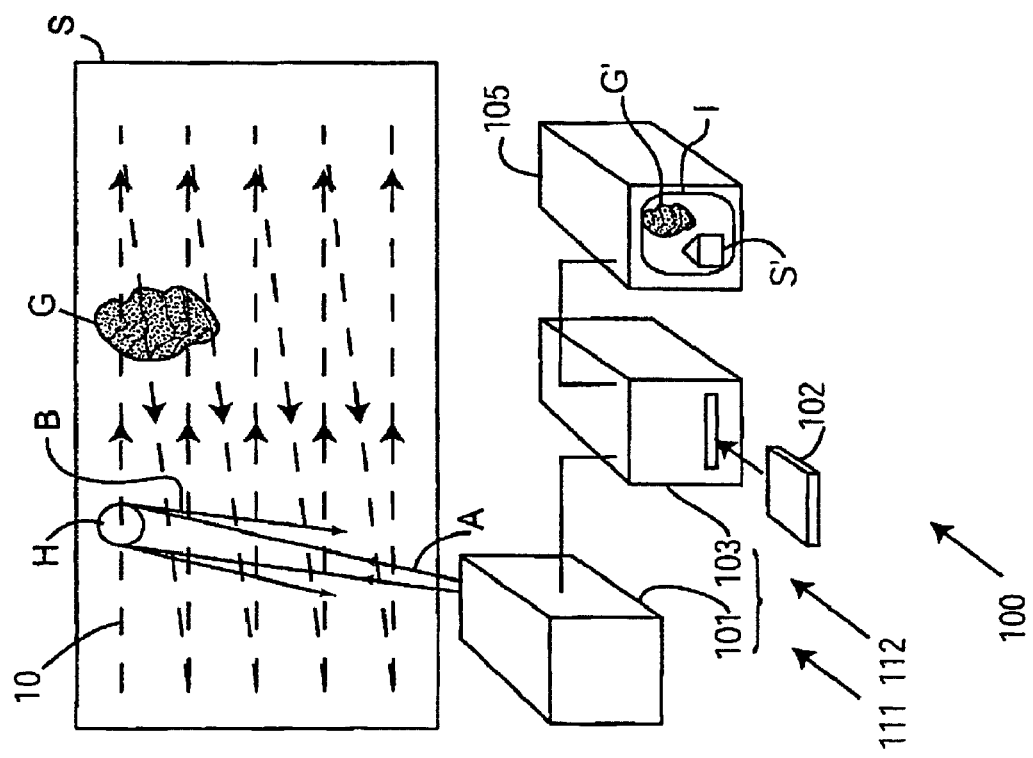

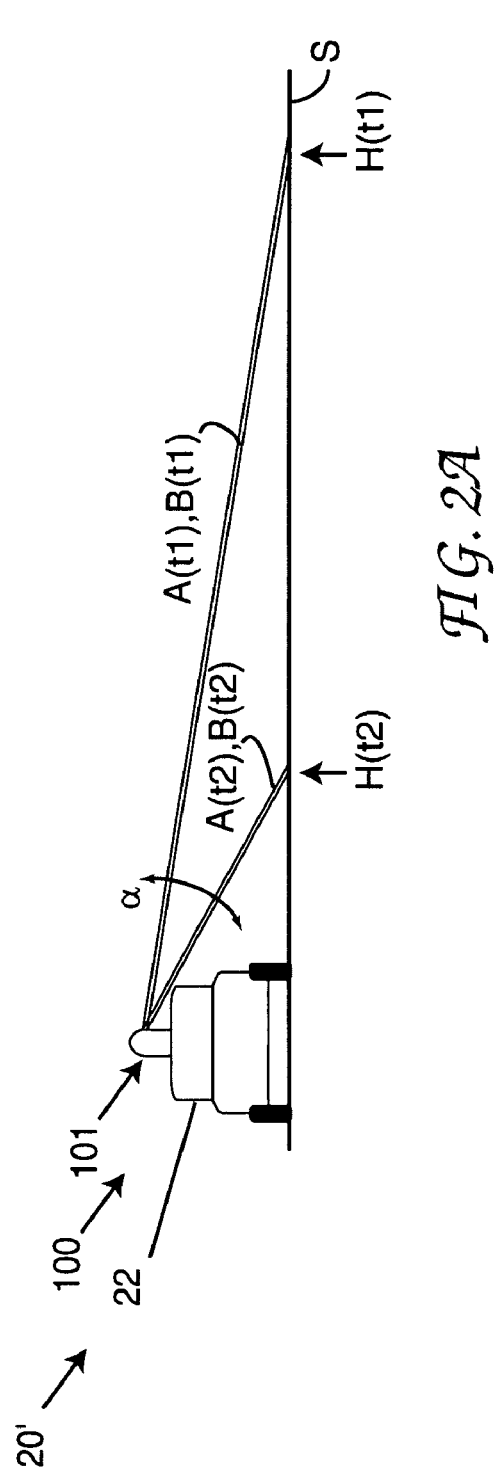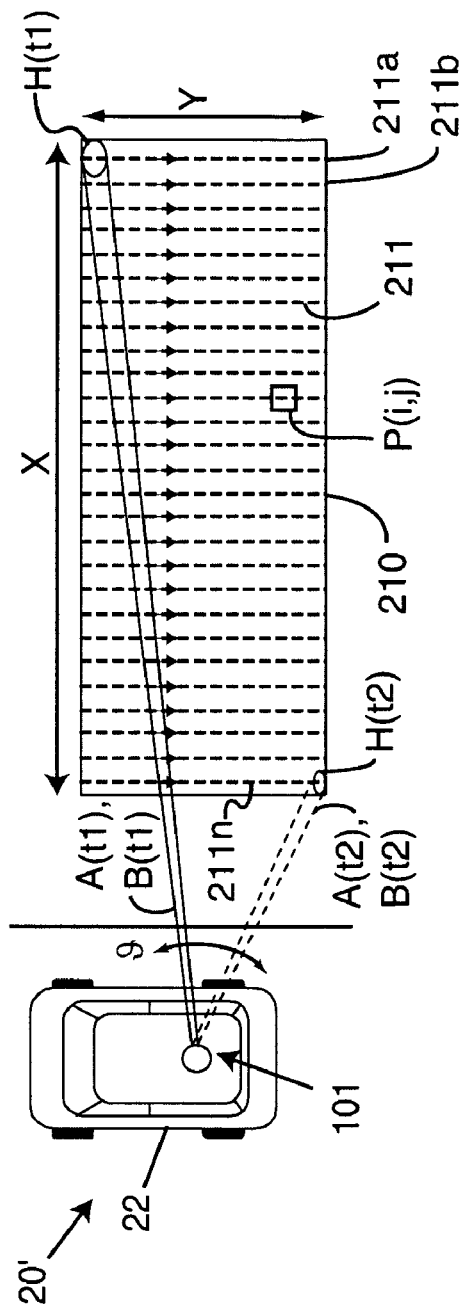

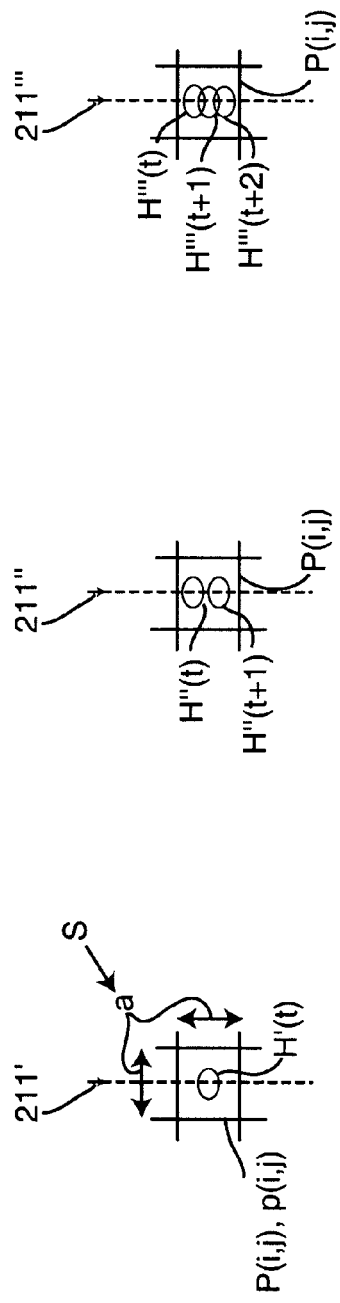
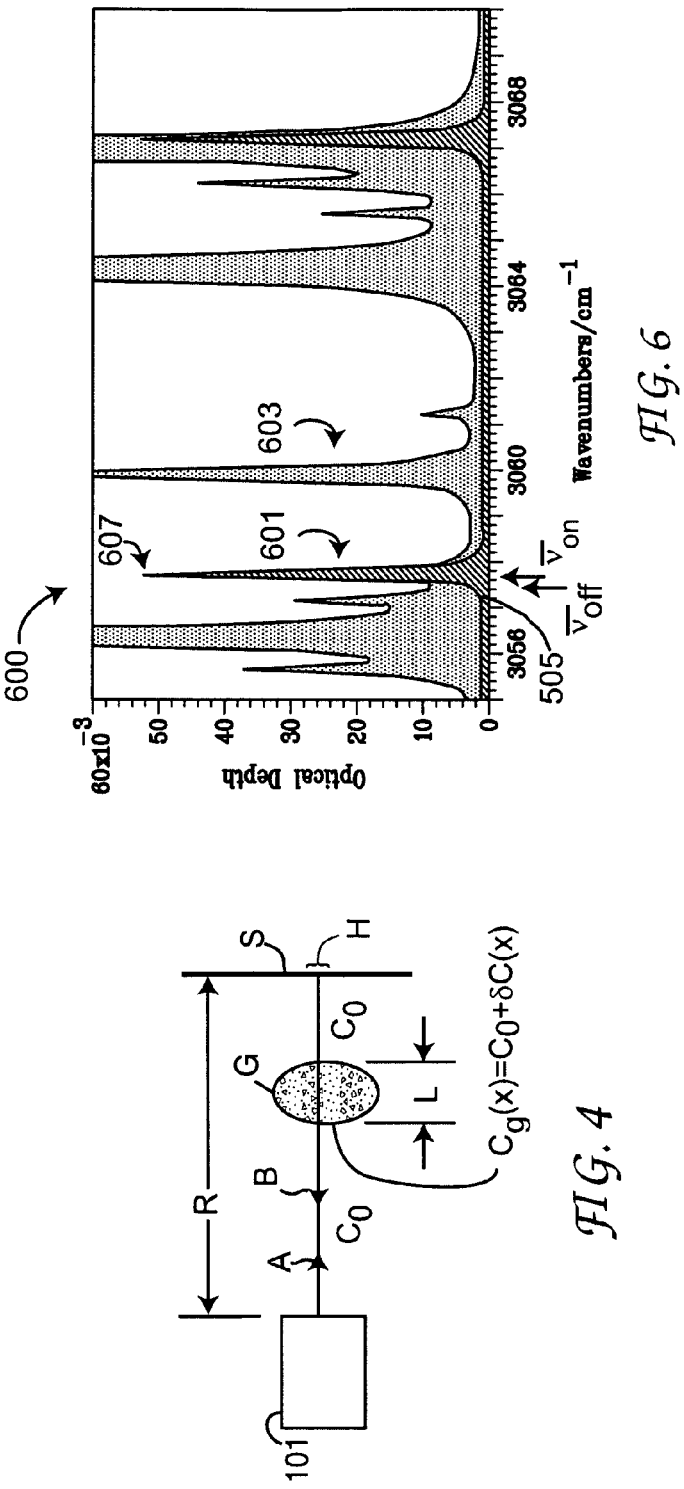
FIG. 2E
FIG. 2D
FIG. 2C
FIG. 6
FIG. 4

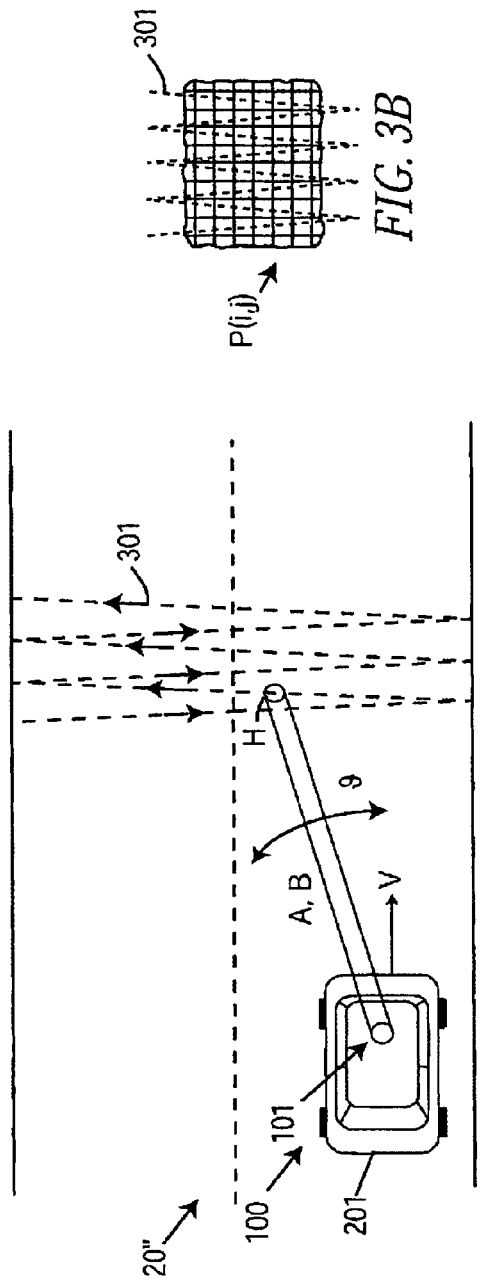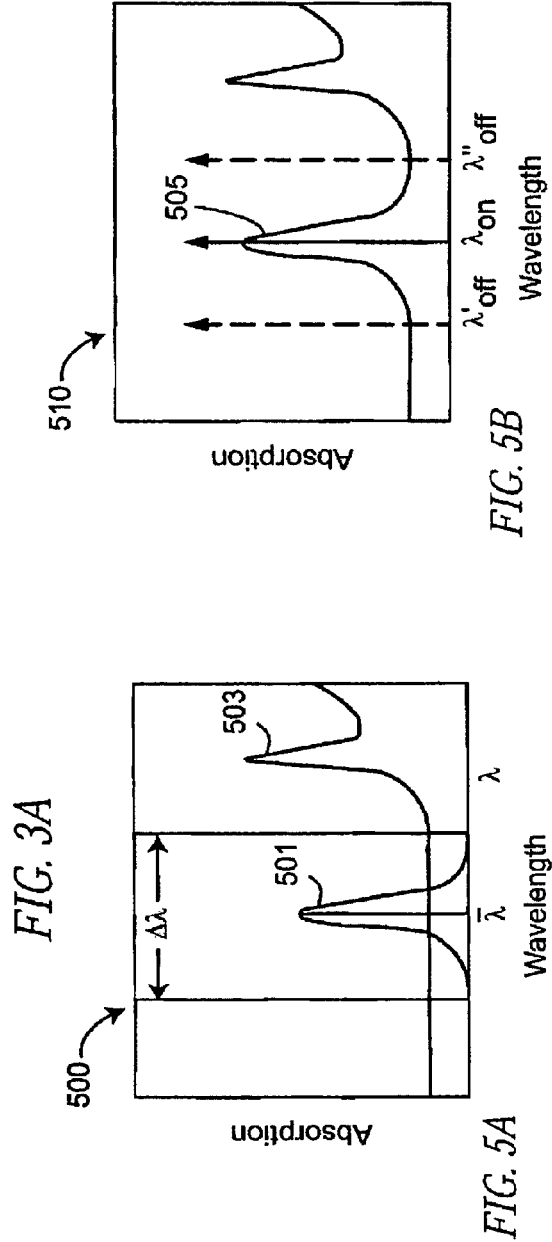

NATURAL GAS LEAK MAPPER

STATEMENT REGARDING FEDERALLY SPONSORED RESEARCH OR DEVELOPMENT

The United States Government has rights in this invention pursuant to Contract No. DE-AC04-94AL85000 between the United States Department of Energy and Sandia Corporation for the operation of Sandia National Laboratories.

BACKGROUND OF THE INVENTION

1. Field of the Invention

The present invention relates to systems to image gases using backscattered absorption gas measurements, and more specifically, it relates to backscatter absorption gas mapping systems for making measurements of gases in the environment.

2. Discussion of the Background

Most gases are invisible to the unaided human eye, particularly at low concentrations. It is thus difficult, and usually impossible, to visually determine the presence and extent of releases of these gases into the environment. The ability to rapidly detect and track hazardous gases in the atmosphere would greatly aid public safety and health, and would be useful in determining the source of gaseous leaks in general. For example, accidental toxic or combustible gas releases can occur from malfunctioning industrial equipment or from accidents involving the transport of bulk hazardous materials. These releases can rapidly diffuse into the surrounding air and move with the prevailing wind. While the safety of the public would be greatly enhanced in such circumstances by the easy determination of the location, extent, and motion of these gases, there is no device that is capable of providing this information. Existing detection technology is labor intensive and costly, requiring manually use of instruments that measure at a single point and in close proximity to the leak source.

Of particular interest is the determination of leaks of natural gas. The natural gas distribution system consists of networks of buried piping in which gas flows at relatively low pressure (15 psi). A leak generated in a distribution line emits natural gas into the surrounding soil where it migrates to the surface and can be detected. The nature of the transport is dependent upon the degree of compaction of the ground. In loose soil, gas is dispersed as it works its way upward to the air interface, where it is released as a diffuse plume. In soil that is more densely packed, the gas may seek low-resistance fissures through which it moves more easily than in the soil body. The boundary between the soil and the outer wall of the pipeline may also serve as such a conduction channel. Gas that has traveled through fissures may be more concentrated at the surface than gas traveling through loose soil—however, the fissure may guide it to a point that is distant from the location of the buried line.

Typically, the gas industry finds methane leaks using time consuming point measurement devices that are moved about in the vicinity of a suspected leak. One type of device has a sampling probe to provide air samples to a hydrogen flame ionization detector (FID). Since methane has a naturally occurring ambient concentration of about 1.5 ppm, the detector is set to produce an alarm for methane concentrations above the ambient concentration of about 1.5 ppm. Once the devices indicate the presence of methane, an operator moves a sampling probe or the entire device to find the source of the leak at the point of highest methane concentration. Depending on the sampling arrangement of the detector, leaks of 1-2 ppm can be detected.

Backscatter absorption gas imaging (BAGI) is one advanced technique that shows promise for remotely producing real-time images of methane and other gases. A BAGI system consists of a light source that produces radiation that is absorbed by a gas of interest and an imaging system that collects the light to produce images of the extent of the gas within an imaged scene. Light is directed towards an area having a solid object (e.g., a wall or the ground) in the imaging system's field of view. The solid object scatters light back towards the camera, and if the gas of interest is present, the light will be absorbed while traveling towards the object and when backscattered from the object to the imaging system. Light that is thus backscattered is imaged, or processed to produce an image, of the scene that can be interpreted by the BAGI system user to determine the presence and position of gas in the environment. A BAGI image, for example, can consist of light and dark regions according to the amount of absorbing gases present. Brighter regions correspond to scenes having no, or small amounts of, absorbing gases, and darker regions correspond to scenes having higher amounts of absorbing gases. By adjusting the wavelength of the BAGI light source to correspond to the spectral absorption features of different gases, BAGI systems can produce images of the extent of these different gases.

Although BAGI systems are able to provide an image of gas locations in the environment, prior art BAGI systems suffer from limitations that prevent them from being generally useful in producing real-time images of low concentrations of a gas naturally present in the environment. Problems in making BAGI measurements are generally related to the difficulties in obtaining backscattered light signals of sufficient strength and quality to differentiate localized gas absorption from the background. Thus, for example, some of the problems include, but are not limited to, variations in the optical properties of backscattering surfaces, scattering of light into collection optics, and detector sensitivity and noise. In addition, BAGI systems that illuminate a scene also have problems due to, for example, variations in laser power and difficulties in providing sufficient power at useful wavelengths of light.

In addition, since the BAGI image is derived from the total amount of absorbing gas along the system's optical path length, the presence of a background concentration is problematic. Thus, for example, at large BAGI system-to-backscattering surface spacing, the background absorption will dominate the absorption and the fugitive emissions will be comparable to the system resolution. Thus the maximum-light source-to-backscattering surface distance will be limited by the background concentration and resolution of the system. In addition, the distance from the light source to the backscattering surface can vary over the imaged scene. The absorption by the gas naturally present in the environment will attenuate the backscattered signal more for areas in the scene for which the backscattering surface is further from the BAGI instrument.

Another problem with prior art BAGI systems is due to "speckle" that results from reflecting a highly monochromatic light off of the uneven surface. Thus while the BAGI beams from the light source to the solid surface can have well defined and stable intensity profiles, the return beam has an speckle pattern resulting in intensity variations that introduce noise to the resulting absorption measurement.

Therefore, it would be desirable to have a method and system that provides a portable system to acquire images of gas in the environment, and thereby enabling the easy detection of leaks among a background of gas, that corrects for variations in the optical path length between different positions on a gas image, and that reduces some of the sources of noise in prior art systems. Such a method and system should be portable, robust, and capable of discriminating leaks of combustible gases from a safe distance.

BRIEF SUMMARY OF THE INVENTION

The present invention overcomes the disadvantages of prior art by providing a system to measure backscattered light and assemble an image by scanning small portions of a scene and reconstructing an image showing the presence of gases of interest. Thus, for example, one embodiment of the present invention includes an optical unit having a light source that is focused into a beam and scanned across a surface. The measurements are processed measurement-by-measurement, and thus can be normalized for laser intensity or other temporal or spatially varying sources of error.

It is one aspect of the present invention to provide a system to present an image of a gas of interest having a background concentration.

It is another aspect of the present invention to provide a system to present an image of a gas of interest having an optical parametric frequency converter to generate light of different wavelengths.

It is yet another aspect of the present invention to provide a system presenting an image of the presence of a gas of interest including an apparatus for determining the distance from the system to the backscattering surface and an absorption measurement. In one embodiment, the distance is used to correct the absorption measurement for a background concentration of the gas of interest. In another embodiment of the present invention, the measured distance is used to correct the intensity of an image of light not absorbed by the gas of interest.

It is one aspect of the present invention to provide a system to present an image of the presence of a gas of interest. In one embodiment, an image of the scene is superimposed on the image of the presence of the gas of interest.

It is another aspect of the present invention to provide an apparatus for providing an indication of the presence of a gas of interest having a background concentration within a scene having a surface. The apparatus includes a backscatter absorption gas measurement system to generate light to illuminate the surface and determine an indication of absorption by the gas of interest within the scene, a range measurement system to determine an indication of the distance from the backscatter absorption gas measurement system to the surface illuminated by the backscatter absorption gas measurement system, and a processor to combine the determined indication of absorption and the determined indication of the distance to provide an indication of the presence of the gas of interest in excess of the background concentration. In one embodiment, the backscatter absorption gas measurement system illuminates with light of a first wavelength not absorbed by the gas of interest, the backscatter absorption gas measurement system measures the intensity of backscattered light of the first wavelength, and the processor combines the measured intensity of backscattered light of the first wavelength into an image of the scene.

It is yet another aspect of the present invention to provide an apparatus for determining the presence of a gas of interest within a scene having a surface. The apparatus includes a backscatter absorption gas measurement system to illuminate the surface with two or more wavelengths of light including at least one wavelength of light absorbed by the gas of interest, and determine absorption by the gas of interest at at least two of the two or more wavelengths, and a processor to accept the determined absorption at the at least two wavelengths and generate an image of the scene indicating the presence of the gas of interest. In one embodiment, the system further includes a range measurement system to determine an indication of the distance from the backscatter absorption gas measurement system to the surface illuminated by the backscatter absorption gas measurement system, and the processor accepts the determined indication of the distance and generates the image from the determined absorption and the determined indication of the distance.

It is one aspect of the present invention to provide an apparatus for determining the presence of a gas of interest within a scene having a surface. The apparatus includes a light source to illuminate the surface at at least one wavelength, at least one detector to measure the intensity of light from the surface at the at least one wavelength, and a processor to determine the distance traversed by light illuminating the surface and to one of the at least one detector, and calculate an indication of the presence of the gas of interest from the measured intensity and the determined distance.

It is yet another aspect of the present invention to provide a method of estimating the amount of a gas of interest in excess of a background amount. The method includes measuring a total amount of the gas of interest corresponding to one portion of an image of a mapping system, estimating the background amount of the gas of interest at the one portion, and subtracting the estimated background amount of the gas of interest from the total amount of the gas of interest for the one portion. One embodiment of the method further includes comparing the results of the subtraction to a model of a plume of excess gas to estimate a maximum gas concentration.

It is one aspect of the present invention to provide a carrier medium carrying one or more computer readable code segments to instruct a processor to implement a estimating the amount of a gas of interest in excess of a background concentration. The method includes measuring a total amount of the gas of interest corresponding to one portion of an image of a mapping system, estimating the background amount of the gas of interest at the one portion, and subtracting the estimated background amount of the gas of interest from the total amount of the gas of interest for the one portion. One embodiment of the method further includes comparing the results of the subtraction to a model of a plume of excess gas to estimate a maximum gas concentration.

These features together with the various ancillary provisions and features which will become apparent to those skilled in the art from the following detailed description, are attained by the exercise device of the present invention, preferred embodiments thereof being shown with reference to the accompanying drawings, by way of example only, wherein:

BRIEF DESCRIPTION OF THE SEVERAL VIEWS OF THE DRAWING

FIG. 1A is a perspective view of one embodiment of the present invention as a gas mapping system, and FIGS. 1B and 1C illustrate the illumination of an area and the collection of light by the system, respectively;

FIGS. 2A and 2B show a top and side view, respectively, of a fixed mobile imager, and FIGS. 2C, 2D, and 2E are three embodiments illustrating the illumination of a surface area;

FIG. 3A is a top view of mobile imager, and FIG. 3B shows a portion of the surface imaged by the mobile imager;

FIG. 4 is another embodiment of backscatter absorption gas mapping system of the present invention;

FIGS. 5A and 5B, respectively, which show the amount of light absorbed through given amounts of an absorbing gas;

FIG. 6 is an absorption spectra for methane;

FIG. 10A is a schematic overall view, FIG. 10A is a schematic top view, and FIG. 10C is a schematic side view.

Figure 7:
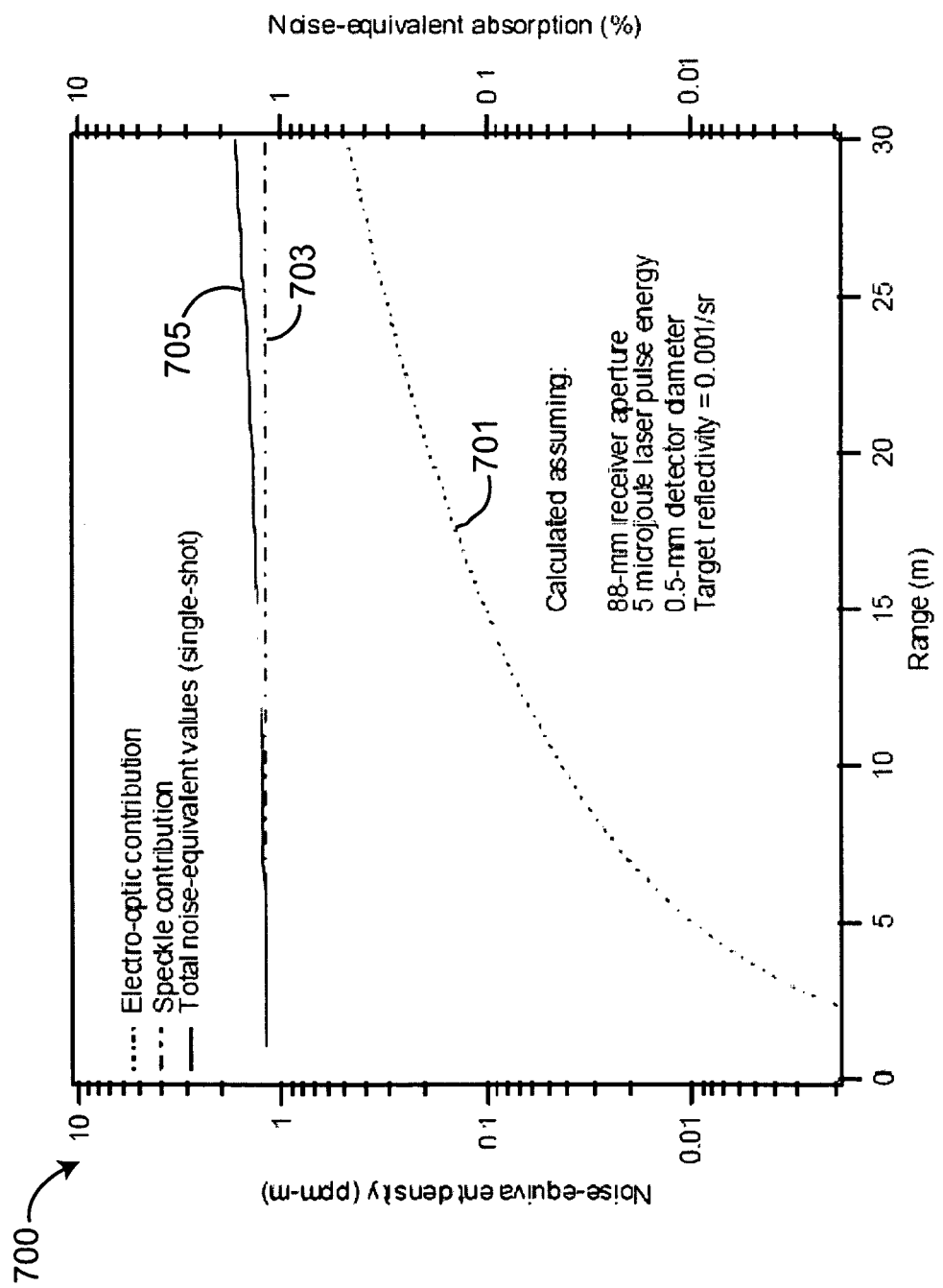
FIG. 7 is a graph showing the results of a calculation of the amount of noise inherent in a backscatter measurement.

Reference symbols are used in the Figures to indicate certain components, aspects or features shown therein, with reference symbols common to more than one Figure indicating like components, aspects or features shown therein.

DETAILED DESCRIPTION OF THE INVENTION

The present invention will now be described in terms of systems that measure gases of interest by making spectroscopically differentiated absorption measurements of laser light backscattered from a surface in a scene and through the gas. The measurements are described herein as including the use of lasers. The term "laser" as used herein is intended to include lasers as well as any other light sources with spectral and brightness properties meeting the requirements presented in this teaching. For example such light sources could include a laser followed by a frequency conversion device or an incandescent beam from a gas discharge source. The light source is capable of operating in a single-wavelength or differential mode and is designed to produce high-quality images even when the system experiences moderate movement or vibration (such as might occur when the system is driven in a vehicle). In addition, the light or beam generated by the laser is intended to include light at wavelengths that are efficiently propagated across the scene, including at least one wavelength of light that is absorbed by a gas of interest, and includes electromagnetic radiation in the ultraviolet, visible, or infrared portions of the spectra, as appropriate.

FIG. 1A is a perspective view of one embodiment of the present invention as a gas mapping system 100. System 100 "maps" a scene using a laser light to interrogate the scene by scanning the light to illuminate portions of a surface of the scene, measuring light from the scene, and providing an image of the scene that includes measurements of light returning to the system. In general, mapping may be accomplished by projecting a beam of light and scanning in two directions over an area (a "point mapper"), or by projecting a line of light and scanning the line perpendicular to the length of the line in one direction over an area (a "line mapper"). In general, the mapper light may include one or more beams of continuous (cw) or pulsed laser light. In some embodiments of the present invention, measurements from more than one wavelength of light are used to interrogate the scene. The multiple wavelengths may either be combined within a single cw or pulsed beam, or alternatively, combinations of the multiple wavelengths may be provided to the scene sequentially, for example in alternately pulsed beams having different spectral characteristics. The present invention, which includes systems and methods that are generally applicable to mapping systems, will be described with reference to several embodiments of a point mapper, that is, a mapper that interrogates a scene by scanning a beam in two directions over a scene. A linemapper BAGI system is described, for example, in commonly-owned U.S. Pat. No. 6,690,472, incorporated herein by reference. It is understood that the discussion of the invention in terms of a point mapper is not meant to limit the scope of the present invention.

Gas mapping system 100 is a backscatter gas absorption mapping system that includes the measurement of a system-to-backscattering surface distance measurement, that is, it includes a backscatter absorption gas measurement system 111 and range measurement system 112. As described subsequently, backscatter absorption gas measurement system 111 includes a light source for illuminating a scene and detectors to measure the intensity of backscattered light. Measurements from backscatter absorption gas measurement system 111 provide an indication of the total amount of an absorbing gas being imaged. Range measurement system 112 includes detectors and/or methods for determining the optical path of light of the backscatter absorption gas measurement system 111. When mapping a gas of interest having a background concentration, a method of the present invention allows system 100 to provide an improved indication of the amount of absorbing gas using the measurements of systems 111 and 112. Thus, for example, in one embodiment of the present invention, the backscatter gas measurement of system 111 determines an integrated concentration of the gas of interest. System 100 calculates the contribution from the background concentration of the gas of interest using the distance measurement of system 112, and then provides an indication of the gas presence that is corrected for the background gas concentration.

More specifically, system 100 includes an optical unit 101, a computer processor 103, and a display 105 to display an image I. The backscatter absorption gas measurement system 111 and range measurement system 112 both use optical measurements and calculations of the measurements in producing an image I. Optical unit 101 generates a scanning light, indicated generally as beam A, for the measurements of systems 111 and 112. In general, beam A, which includes light for both systems 111 and 112, can be one or more light sources within optical unit 101. In one embodiment of the present invention, a single light source generates light for both systems 111 and 112. In another embodiment of the present invention, optical unit combines the light from two or more light sources into beam A.

System 100 may be used to determine the presence of certain gases between the system and a surface. As shown in FIG. 1A, the scene, which is not part of the present invention, includes, for example, a surface S and that has a plume G of an absorbing gas. In addition to scanning beam A, optical unit 101 receives and measures properties of light from the scene. Computer processor 103 accepts the light measurements from optical unit 101 and processes the measured properties of the light. Processor 103 correlates the location of the interrogating light beam relative to the scene and formats the measurements such that image I is useful in determining the location of a detected gas within a scene. Display 105 accepts information, including processed light measurement, and for display as image I. In one embodiment of the present invention, carrier medium 102 contains programming instructions processor 103 to execute the methods of the present invention, for example some or all of the instructions described with reference to the present invention.

In one embodiment of the present invention, display 105 presents image I, which includes an indication of the presence of a gas of interest within a scene being mapped, and may alternatively include a superimposed image of surfaces within the scene being mapped. Thus, for example, FIG. 1 shows image I as indicating the extent of the gas of the gas of interest G as an image G' on display 105. FIG. 1 also shows the alternative presentation of an image S' of surface S within the scene being mapped. The presentation of image I as the superposition of images S' and G' allowing a user to visually identify the location of the gas of interest within the mapped scene.

Optical unit 101, processor 103, and display 105 may be located near one another, or may be physically separated. In addition, the functions of the optical unit 101, processor 103, and display 105 may be distributed among the components shown, for example by having all or part of processor 103 within optical unit 101 or display 105, or by having an optical unit that includes physically displaced transmitting and receiving units. Also, the connection between optical unit 101, processor 103, and display 105 may be wireless, and may include other connections or not include direct connections, for example, as over a computer network.

Optical unit 101 includes optical components to generate light and to receive and measure certain properties of light, where the components may include but not limited to lenses, mirrors, prisms and beam splitters, and electro-optical components such as lasers and optical detectors such as photodetectors. In system 100, for example, optical unit 101 includes optical components to generates a laser light beam A and direct the beam along two directions to scan a scene. The intensity and wavelengths of beam A is, in general, selected to be efficiently transmitted through the gases over the roundtrip distance between system 100 and a solid surface, and to be detected by the system as backscattered light. While the surface S is shown as being planar in FIG. 1A, the surface can, in general, be a surface of any shape or orientation relative to optical unit 101. Thus, for example, the scene can include one or more objects with solid surfaces, and, for example, can include an oblique view of the ground having buildings. Also shown in FIG. 1A is an area H of surface S illuminated by beam A. System 100 directs beam A to illuminate a spot, or area H of surface S. The area H is moved, or scanned, by system 100 to cover some portion of the surface. As one example of the path taken by area H in scanning surface S, system 100 controls the scanning to trace out the zigzag pattern illustrated dashed line 10 of FIG. 1A.

Optical unit 101 also receives light from the general direction of surface S, including light from beam A that illuminates area H and is reflected (or 'backscattered') as a backscattered beam B towards optical unit 101. Thus, for example, during propagation, beam A interacts with gases between optical unit 101 and surface S, and a portion of the light is reflected from area H towards the system as backscattered beam B, which further interacts with the gases. Optical unit 101 measures properties of beam B including, but not limited to, wavelength dependent measurements of beam intensity and the timing of pulses.

FIGS. 1B and 1C illustrate the illumination of an area H (FIG. 1B) and the collection of light by optical unit 101 directed at area H' (FIG. 1C). FIG. 1B shows beam A projected onto area H and a distance R, which is the length of the optical path from optical unit 101 to a particular area H. In general, the distance, or optical path, R varies with time as area H scans to different locations of surface S according to the orientation of the surface relative to system 100. FIG. 1C shows the instantaneous field-of-view IFOV of the receiving optics of optical unit 101 as including an area H' of surface S, and the extent of backscattered beam B from area H. In general, optical unit 101 receives light from within instantaneous field-of-view IFOV, as defined by the receiving optics, which may include but is not limited to blackbody radiation from, or light reflected from other sources onto, area H', and scattering or emissions from light within the IFOV. It is preferred that the IFOV efficiently collect beam B. In the embodiment of system 100, backscattered light from optical unit 101 propagates a total, round-trip optical path of a distance 2R through the gas being investigated: a distance R from optical unit 101 to area H, and a distance R from area H to optical unit 101. In general the light source and receiver may be at different distances from the backscatter surface, and the round trip distance would differ according to the path of the backscattered light.

In the embodiment of the present invention illustrated in FIG. 1C, system 100 moves the IFOV of optical unit 101 to follow the illuminated area H. Thus, for example, the IFOV, as determined by the collection optics, collects light from an area H' of surface S that is near area H. In one embodiment, area H' is larger and includes area H, thus minimizing variations due to the beam profile of beam A. In one embodiment of the present invention, the collection optics are coaxial with the illumination optics and that have a larger divergence angle, providing an area H' that changes according to area H and includes at least the area H. Alternately, H' may be equal to or smaller than the area H.

In one embodiment of the present invention, optical unit 101 generates and measures light for backscatter absorption gas measurement system 111 at two wavelengths. Specifically, beam A includes light at two wavelengths and the optical unit measures light intensity at the two wavelengths. A discussion of the use of multiple wavelengths of light for making a differential absorption measurement is found, for example, in U.S. Pat. No. 6,690,472. In a system that performs differential absorption measurements, it is preferred that one wavelength of beam A is well absorbed by the gas to be detected and a second wavelength of beam A is less well absorbed by the gas to be detected. Several embodiments of the present invention provide the multiple wavelengths in sequentially generated multiple beams. Thus in one embodiment, beam A is two sequentially generated pulsed beams having different spectral qualities, for example, a first beam being primarily light of one wavelength followed by a second beam being primarily light of a different wavelength. When measurements of backscattered light from sequential beams are used in one method of determining the presence of a gas of interest, the differences in time and space between the first and second beams should be such that the gases and surfaces encountered by the beams have differences in optical characteristics that are not detectable, that is, variations in gas concentration and surface reflectivity that are within the acceptable level of signal noise. Alternatively, optical unit 101 may generate beam A that has optical characteristics to measure more than one gas, or that is tunable to be selectively absorbed by one gas or another. In another alternative embodiment, optical unit 101 generates light at one wavelength for a single wavelength absorption measurement.

In one embodiment of the present invention, range measurement system 112 determines a distance from a measure of the time between the generation of a pulse of light in beam A and the return as backscatter beam B. System 112 determines the round-trip time of flight (RTTOF) of the beam from transmission from the system to the return after backscattering, which, using the speed of light, is then used to estimate the distance traversed by the beam. The generation time of beam A may either be obtained from a reference electrical signal in the light source generating beam A, or may be a direct measure of beam A intensity from a detector. In general, the pulse for the distance measurement may be the same or different from the light used for making the absorption measurement. Thus, for example, the portion of beam A used by range measurement system 112 may be one of the portions of the beam used for the measurement of system 111, or may be used only for the distance measurement. In various embodiments of the present invention, which are not meant to limit the scope of the present invention, the light used in determining the RTTOF is the same as a pulsed beam used for making an absorption measurement, or is a pulsed beam that is not used for making an absorption measurement, and that is either simultaneous with and is spectrally separable from the beam of the absorption measurement, or is separated in time from the absorption measurement. Alternatively, system 112 may contain a light source separate from that of system 111 having light that is combined with the system 111 to form beam A. In an alternative embodiment, range measurement system 112 measures the range by imparting a modulation of the amplitude, wavelength, or phase of the outgoing light and detecting this modulation on the backscattered signal.

System 100 thus generates a beam A and measures returning light at at least two wavelengths of light. The measurements of at least some of the light are spectroscopically differentiated between the wavelengths. The differentiation may occur at either upon transmitting beam A or upon receiving the backscattered light. Thus, for example, individual wavelengths of light may be transmitted through the gas, or, alternatively, multiple wavelengths of light may be transmitted through the gas and filters may be used to differentiate between different wavelengths at the receiver. In one embodiment of the present invention, beam A is a continuous or pulsating beam that contains the two wavelengths ($\lambda_1$ and $\lambda_2$). In one embodiment of the present invention, the RTTOF measurement of system 112 is measured from pulsed light at $\lambda_1$ or $\lambda_2$. The RTTOF measurement may alternately be performed on a pulsed light of a third wavelength, for example $\lambda_3$, that is transmitted along with, or separately from, one or both of $\lambda_1$ or $\lambda_2$.

To provide an image of a gas of interest, system 100 is required to produce an image of sufficient quality to allow gases to be imaged under the required operating conditions. Thus it is important that system 100 discriminate light from backscattered B from other sources of light which may include, but is not limited to, other sources of radiation within the field-of-view of optical unit 101, such as blackbody radiation or scattering of light from surface S or gases between the system and the surface. It is also important that a required minimum detectable concentration of a gas to be detected produces a signal that is greater than the background noise.

FIGS. 2A-2E and 3A-B depicts another embodiment of backscatter absorption gas mapping system 100, which may be generally similar to the embodiment illustrated in FIG. 1, except as further detailed below. Where possible, similar elements are identified with identical reference numerals in the depiction of the embodiments of FIGS. 1, 2 and 3. As shown in FIGS. 2A-2B and 3A, system 100 has optical unit 101 mounted on a vehicle 22 for the mapping of a scene that is either fixed or moving relative to the system on a mobile imager 20' as described subsequently. Display 105 is preferably in the passenger compartment to allow a user to detect easily the presence of a gas of interest. In addition, the image I may be transmitted wirelessly to a remote location.

FIGS. 2A and 2B show a top and side view, respectively, of a fixed mobile imager 20' is parked on surface S. System 100 projects and scans beam A in a horizontal plane, as indicated by the arrow labeled δ, and in a vertical plane, as indicated by the arrow labeled α. As the time progress from one time t1 to a later time t2, beam A is swept from the position indicated as A(t1) to the position indicated as beam A(t2) to illuminate corresponding areas H(t1) and H(t2). Beam A scans an area 210 of surface S having dimensions X and Y, and proceeds along dashed lines 211 including lines 211a, 211b, . . . , 211n. At the end of each scan line beam A is directed to the beginning of the next line. The return scan is not shown in FIG. 2B, as system 100 does not collect backscattered light on the return scan when operated as imager 20'. At time t=t1, beam A is at one corner of area 210 at the beginning of line 211a. Lines 211 are scanned sequentially, and at time t=t2, beam A is at the opposite corner of area 210 at the end of line 211n. As beam A is scanned across surface S, light is backscattered as beam B towards system 200 as indicated in FIGS. 2A and 2B. Since system 100 is sitting above and to the side of area 210, the distance from system 100 to each area H varies with the scan of area 210.

System 100 maps, or formats, measurements of beam B into an image based on the instantaneous position of beam A. Each pixel of image I, indicated as an arbitrary pixel p(i,j), thus has a corresponding area on surface S, indicated, for example, as the corresponding surface area P(i,j) as shown in FIG. 2B. Depending on the characteristics of the scanning of beam A, such as variations in the beam position and wavelength, one or more areas H may fall within a particular surface area P(i,j). In general, there may be more than one beam incident on an area P(i,j), and more than one measurement obtained per pixel p(i,j), thus allowing for signal averaging. A particular surface area P(i,j) is shown in FIG. 2B, along with the corresponding pixel location. The shape of area P(i,j) is shown schematically as being square and measuring a on a side.

In the embodiment illustrated in FIGS. 2A and 2B, system 100 of imager 20' interrogates a rectangular area of X=100 ft by Y=15 ft. This area may be, for example, the area between the main and the meter set (or as close to the meter set as possible). In one embodiment, each measurement area P(i,j) measures a=10 cm and a data collection time of 3 minutes, complete surveillance of this area requires 13,500 measurement areas P(i,j) at 13.3 ms per measurement, for a data collection rate of 77 Hz. Thus, for example, in one embodiment beam A is a cw beam scanned at a rate to allow a 77 Hz data collection rate, while in an alternative embodiment beam A is a pulsed beam that pulses at 77 Hz, or that pulses at a frequency greater than 77 Hz to allow more than one measurement to be made per area P(i,j).

Three embodiments of imager 20' are shown as having different illuminations of surface area P(i,j) in FIGS. 2C-2E. These embodiments are meant to illustrate three of the many possible embodiments of the present invention, and are not meant to limit the scope of the invention. In each of the following three embodiments, measurements at three wavelengths of light are used to determine the presence of a gas of interest-2 wavelengths for the absorption measurement and one for the RTTOF measurements. In the embodiment of FIG. 2C, measurement area P(i,j) is illuminated by beam A that includes three simultaneous or sequentially produced beams that illuminate the same area H'(t)on scan line 211'. The backscattered light is analyzed to determine the presence of a gas of interest within the round-trip optical path from system 100 to the portion of surface corresponding to pixel p(i,j).

In the embodiment of FIG. 2D, measurement area P(i,j) is an illuminated portion along a scan line 211" includes an area H"(t) and an area H"(t+1). Beam A includes two alternating beams, each with two wavelengths—one for an absorption measurement and one for a RTTOF measurement. Thus, for example, area H"(t) is illuminated with a first of two wavelengths for making an absorption measurement and a third wavelength for making an RTTOF measurement, and area H"(t+1) is illuminated with a second of the two wavelengths for making an absorption measurement and the third wavelength for making the RTTOF measurements. In an alternative embodiment of the present invention, more than two pair of alternating beams illuminate area P(i,j), thus allowing for more than one measurement per corresponding pixel p(i,j) to be obtained for signal averaging of the measurements.

In the embodiment of FIG. 2E, beam A includes three sequential beams, one of each intensity, that each illuminate sequential areas H'"(t), H'"(t+1), and H'"(t+2). The backscattered light from areas H'"(t), H'"(t+1), and H'"(t+2) can be analyzed to determine the presence of a gas of interest within the round-trip optical path from system 200 to measurement area P(i,j). In an alternative embodiment, not shown, measurement area P(i,j) is illuminated by two or more sets of three sequential beams, allowing for signal averaging of the measurements.

Alternatively, the beams of FIGS. 2C-2E may not include light for making an RTTOF measurement, or may include a single pulsed beam for making a combined single absorption measurement and an RTTOF measurement. Such an alternative embodiment would not permit the determination of a distance measurement, but would allow for averaging more than one absorption measurement per pixel.

FIG. 3A is a top view of mobile imager 20". Vehicle 201 is moving along a roadway S with a velocity V. With imager 20" moving, and beam A scans side-to-side in a horizontal plane, as indicated by the an-ow labeled δ. At the end of each scan line beam A is directed to the beginning of the next line. The return scan is not shown in FIG. 2B, as system 100 does not collect backscattered light on the return scan when operated as imager 20'. The resulting path traced by beam A is indicated as tracing a zigzag path 301 across the roadway and generating a backscattered beam B.

In the embodiment of FIG. 3A, a roadway width of 30 ft is scanned with a measurement area a=10 cm on a side. At this sample size, 90 measurement areas must be made across the width of the road. The measurements must be measured quickly enough to allow the next row of measurement areas on the road, which is a=10 cm away, to be measured on the next scan. To ensure that the distance between points in the driving direction is no greater than a=10 cm, the vehicle must not move more than a/2=5 cm during a single horizontal sweep. Thus, the time per point is dependent upon the vehicle speed V (in miles per hour—MPH) as:

$$\Delta t = \frac{0.11}{V(MPH)}.$$

Thus, a vehicle traveling 30 MPH must make a point measurement in 3.7 msec, or the point measurement rate must be 273 Hz. Thus, for example, in one embodiment beam A is a cw beam scanned at a rate to allow a 273 Hz data collection rate, while in an alternative embodiment beam A is a pulsed beam that pulses at 273 Hz, or that pulses at a frequency greater than 273 Hz to allow more than one measurement to be made per area P(i,j). FIG. 3B shows several pixels of a portion of image I generated by system 100 of imager 20" and path 301. System 100 correlates the position of location L with the view from the moving vehicle, and generates an image accordingly.

The scanning and formatting of image I is controlled by optical unit 101 and processor 103, which together direct beam A according to the mode of operation of imager 20, including, but not limited to a fixed imager 20' and a mobile imager 20". In particular, the formatting of image I may include the speed of vehicle 22 as well as any variable motion of the vehicle or other movement of optical unit 101.

Systems and Methods for Generating Images

The methods for processing signals from the measurements are illustrated with reference to FIG. 4, which shows system 100 directing laser light beam A having an optical path, or distance, R to area H of surface S. The distance R includes a background concentration $C_0$ of a gas of interest, and also includes a gas plume G of the gas of interest, having thickness L, and having a concentration $C_g(x)=C_0+\delta C(x)$, that is the concentration $\delta C(x)$ is deviation of the concentration from the background concentration. When beam A is directed through plume G and towards surface S, a portion of the light is backscattered from area H is received by unit 101 as beam B, also having an optical path R. The received light is converted to signals in optical unit 101, and the signals are processed and assembled into an image I for viewing on display 105 to show the view of surface S with the location of the plume highlighted. Image I shows an indication of the presence of a gas of interest on image above a background concentration.

The use of system 100 in determining the presence of an absorbing gas is illustrated, in general, by way of the absorption plots 500 and 510 of FIGS. 5A and 5B, respectively, which show the amount of light absorbed through given amounts of gas. Plot 500 shows absorption curves 501 and 503 for individual components of a gas through which measurements are to be made. Curve 501 is peaked about a wavelength $\bar{\lambda}$ with a wavelength width of $\Delta\lambda$. Curve 503 shows the absorption due to background gases, for example other atmospheric gases, that are within the measurement having concentration $C_{atm}$. Plot 510 shows absorption curves 505 for a gas mixture containing all of the gas components of plot 500. Also indicated in plot 510 are several wavelengths of light useful in interrogating the gas mixture including, but not limited to an "on-wavelength" $\lambda_{on}$ that is near the absorption peak of the gas of interest (for example near the peak wavelength $\bar{\lambda}$), and an "off-wavelength" $\lambda_{off}$ that is away from the absorption peak, for example at or near $\lambda'_{off}=\bar{\lambda}-\Delta\lambda/2$ and $\lambda''_{off}=\bar{\lambda}+\Delta\lambda/2$.

System 100 includes lasers to generate beam A including wavelengths $\lambda_{off}$ and $\lambda_{on}$ and beam deflection optics to scan the beam, as well as optics to gather backscattered light and detectors to convert the gathered light into generate electrical signals, $S_{on}$ and $S_{off}$, that are proportional to the intensity of backscattered light beam B at the on-and off-wavelengths, respectively. Thus, for example, $S_{on}$ is proporational to the intensity of backscattered light at $\lambda_{on}$ and $S_{off}$ is proporational to the intensity of backscattered light at $\lambda_{off}$, for example $\lambda'_{off}$ or $\lambda''_{off}$. Alternatively, $S_{off}$ is an average of the intensity of backscattered light at two or more off-wavelengths, such as $S_{off}=(S_{off'}+S_{off''})/2$, where $S_{off'}$ is the backscattered intensity at $\lambda'_{off}$ and $S_{off''}$ is the backscattered intensity at $\lambda''_{off}$. The averaging of signals is useful for correcting for wavelength-dependent reflectivity of back-scattering surfaces.

As one example of the present invention, wavelengths $\lambda_{on}$ and $\lambda_{off}$ alternate between one on-and one off-wavlengths, such as $\lambda_1$ and $\lambda_2$, respectively, of system 100. Alternatively, system 100 may alternate between one on-wavelength and two off-wavelengths, or may project the wavelengths together or in different combinations. By mapping surface S from measurements at many individual areas H, use of mapper allows for correcting the determination of the presence of gases in the resulting image for other effects, such as point-to-point variations in laser intensity, surface reflectance, speckle patterns, and effects due to the variation in distance from the system to the reflecting surface.

Several embodiments of the present invention includes a method of calculating the presence of the gases of interest using the signals $S_{on}$ and $S_{off}$, and alternatively also using a measure of the distance R from system 100 to the backscatter surface. The following discussion presents a mathematical formulation useful in implementing all or part of one or more of the methods of determining gas presence. In particular, while the measurements are shown as being used in particular functional forms to determine or quantify the presence of a gas being measured, it is understood that other functional forms, derived using similar or different methodologies, may be derived that relate the measurement to quantities of the presence of gases.

Let the intensity of the transmitted beam, for example beam A leaving optical unit 101, at wavelength $\lambda$ be $I_\lambda$, and the corresponding backscattered signal of beam B at the optical unit be $S_\lambda$, as generated, for example, by an optical detector output such as a photodetector output. One relationship between $I_\lambda$ and $S_\lambda$ is given by:

$$S_\lambda = c_\lambda \, I_\lambda \, e^{-\alpha_\lambda},$$

where $c_\lambda$ is, in general, a wavelength dependent system constant for a given range that depends, in part, on the optics, detector response, distance to the backscatter surface, and reflectance of the backscatter surface, such as area H, and $\alpha_\lambda$ is the wavelength dependent absorbance of the gasses within the optical path of beams A and B. Further, let the absorbance be modeled as the sum over all the gas species i integrated over the optical path as:

$$\alpha_\lambda = 2 \sum_i \left[ \int_{x=0}^{R} k_{i,\lambda} C_i(x) \, dx \right],$$

where the factor 2 accounts for the double pass of the incident and backscattered light through the, x is a distance along the optical path of beam A from system 100 to area H from x=0 at system 100 to x=R at area H, $k_{i,\lambda}$ is the concentration normalized absorption coefficient of gas i at wavelength $\lambda$, (with units, for example, in $ppm^{-1}m^{-1}$), and $C_i(x)$ is the concentration of gas i in the optical path.

The summation in the previous equation may be separated into a first term for the gas of interest, with subscript "g," and a second term for the remaining gases, excluding any gas of interest as:

$$\alpha_\lambda = 2\left[ \int_{x=0}^{R} k_{g,\lambda} C_g(x) \, dx \right] + 2 K_\lambda R,$$

where $K_\lambda$ as an attenuation coefficient of all of the gases, except the gas of interest, at wavelength $\lambda$, defined as:

$$K_\lambda = \sum_{i \neq g} \left[ \int_{x=0}^{R} k_{i,\lambda} C_i(x) \, dx \right] \Big/ R.$$

where the subscript i≠g indicates that i is not equal to g, the gas of interest. For wavelengths that are off-wavelength ($\lambda$="off"), the gas of interest does not absorb light, $k_{g,off}=0$, and the off-wavelength absorbance is:

$$\alpha_{off} = 2 K_{off} R.$$

For wavelengths that are on-wavelength ($\lambda$="on"), the on-wavelength absorbance is:

$$\alpha_{on} = 2 k_{g,on} \overline{CR} + 2 K_{off} R,$$

where the integrated concentration for the gas of interest over the optical path is given by:

$$\overline{CR} = \int_{x=0}^{R} C_g(x) \, dx, \tag{1}$$

The equation for $S_\lambda$ may be written for the on- and off-wavelengths, and, assuming that $c_\lambda$, $I_\lambda$ do not vary between the on- and off-wavelengths and that the optical properties of the background gases do not vary, $K_{on}=K_{off}=K$, may be combined with the equations for $\alpha_{off}$ and $\alpha_{on}$ to give:

$$S_{off} = c_{off} I_{off} \, e^{-\alpha_{off}} = c \, I \, e^{-2K_{off}R} \text{ and}$$

$$S_{on} = c_{on} I_{on} \, e^{-\alpha_{on}} = c \, I \, e^{-2K_{off}R - 2k_{g,on}\overline{CR}},$$

which can be arranged to give:

$$\overline{CR} = -\frac{1}{2 k_{g,on}} \ln\left[ \frac{S_{on}}{S_{off}} \right]. \tag{2}$$

One embodiment of the present invention evaluates an indication of the presence of the gas of interest from the estimate of the integrated concentration of the absorbing species along the optical path, $\overline{CR}$, as provided by Equation (2), measurements of $S_{on}$ and $S_{off}$, and an estimate of $k_g$ at the on-wavelength. As disscussed above, the measurement $S_{off}$ can either be at a single off-wavelength or can be an average of two or more off-wavelengths.

In an alternative embodiment of system 100, optical unit 101 measures of the intensity of the transmitted beam A, as $N_\lambda$. The quantity $N_\lambda$, for example, can be an energy measurement from all or part of beam A. Using $N_\lambda$, it is not necessary to assume that $I_\lambda$ is the same for the on- and off-wavelengths as in Equation (2). Assuming that $I_\lambda = c' N_\lambda$, where c' is a constant detector response function, Equation (2) can be re-derived, by replacing $S_{on}$ and $S_{off}$ with $S_{on}/N_{on}$ and $S_{off}/N_{off}$, respectively, as:

$$\overline{CR} = -\frac{1}{2k_{g,on}} \ln\left[\frac{S_{on}/N_{on}}{S_{off}/N_{off}}\right]. \quad (2')$$

Alternative embodiments of the present invention normalize one or more measurements of the backscattered light by the intensity of beam A to eliminate or reduce variations in laser intensity, as is shown in Equations (2) and (2'). Thus, for example, in any of the following methods, variations in the backscatter signal $S_\lambda$ may be reduced by normalizing $S_\lambda$ by the intensity of the beam that produced the backscatter signal, that is, $S_\lambda/N_\lambda$. Mapping systems of the present invention, including but not limited to system 100 have an advantage over non-mapping, or imaging systems, in that it is relatively easy to normalize each pixel of an image for variations of laser intensity by normalizing each measurement.

Another estimation of the presence of a gas of interest is an average concentration. Assuming that the distance R can be independently estimated or determined, then Equation (2) can be rearranged to give the average concentration along the optical path, $\overline{C}$, as:

$$\overline{C} = \frac{\overline{CR}}{R} = -\frac{1}{2Rk_{g,on}} \ln\left[\frac{S_{on}}{S_{off}}\right]. \quad (3)$$

One embodiment of the present invention evaluates an indication of the presence of the gas of interest from the estimate of the integrated concentration of the absorbing species, $\overline{C}$, from Equation (3), measurements of $S_{on}$ and $S_{off}$, and estimates or measurements of both $k_g$ at the on-wavelength, and R.

Another estimate of the presence of a plume of a gas of interest may be obtained for a gas having a background concentration. Assuming that the gas of interest is present at a background concentration, $C_0$, over the optical path and a second, varying concentration, $\delta C(x)$ in excess of the background over the localized position of the plume, Equation (1) can be rewritten as:

$$\overline{CR} = \int_{x=0}^{R} C_g(x)dx = C_0 R + \int_{x=0}^{R} \delta C(x)dx = C_0 R + \overline{\delta CL}, \quad (4)$$

where $\overline{\delta CL}$, the integrated plume concentration of the gas of interest in excess of the background, is obtained from:

$$\overline{\delta CL} = -\left[\frac{1}{2k_{g,on}} \ln\left[\frac{S_{on}}{S_{off}}\right] + C_0 R\right]. \quad (5)$$

The logarithm term in Equation (5) represents a differential absorption measurement term, and the term in Equation (5) with R is a correction due to the presence of background gases. One embodiment of the present invention evaluates an indication of the presence of the gas of interest from the estimate of the integrated plume concentration, $\overline{\delta CL}$, from Equation (5), measurements of $S_{on}$ and $S_{off}$, and estimates or measurements of $k_g$ at the on-wavelength, $C_0$, and R.

For leak sources we expect a sharp decrease in gas concentration from the source of a leak over a small distance. If the plume is localized to within a known depth, L, then the average excess concentration in the plume, $\overline{\delta C}$, can be calculated as:

$$\overline{\delta C} = \frac{\overline{\delta CL}}{L},$$

and one embodiment of the present invention evaluates an indication of the presence of the gas of interest from the estimate of the average excess concentration of the absorbing species as:

$$\overline{\delta C} = -\frac{\left[\frac{1}{2k_{g,on}} \ln\left[\frac{S_{on}}{S_{off}}\right] + C_0 R\right]}{L}. \quad (6)$$

In several embodiments of the present invention, system 100 includes devices or methods for optically determining the distance 2R using RTTOF measurements. Measurements of R obtained from this measurement may be used in any of the methods described herein for obtaining a determination of the presence of a gas of interest. Alternatively, measurements of R may be obtained at locations corresponding to some of the absorption measurements, and may be interpolated or extrapolated for nearby areas H.

The RTTOF measurement is based on the relationship between the distance between two locations and the time required for light to traverse the distance between the locations. Assuming that the speed of light, $c_L$, is constant in the environment being probed, the round trip distance, R is related to the time required for light to traverse the distance, $\Delta t$, by: $R = c_L/(2 \Delta t)$. In one embodiment of the present invention, optical unit 101 included photodetectors that intercept a portion of beam A and some or all of beam B. Processor 103 receives time dependent photodetector output and analyzes the output to determine $\Delta t$. In one embodiment, the intensities of one or both of the photodetectors are normalized to a peak intensity so that the measurement of $\Delta t$ is less dependent on the signal strength. In another embodiment of the present invention, the timing of beam A is obtained from electronics that generate the beam, for example a trigger output from a laser of optical unit 101.

An estimate of maximum gas concentration in a plume may be obtained from a model of the gas concentration profile in the plume. Assuming that the concentration of $C_g$ in excess of the background concentration within the plume decays exponentially from a maximum concentration, $C_{max}$, over a distance L as:

$$\delta C(x) = C_{max} \exp(-x/L), \quad (7)$$

the integrated plume concentration is:

$$\overline{\delta CL} = \int_0^L \delta C(x)dx = C_{max} L \int_0^L e^{-\frac{x}{L}} d\frac{x}{L} = 0.632 C_{max} L, \quad (8)$$

and the average excess concentration in the plume, $\overline{\delta C}$ is given by:

$$\overline{\delta C} = \frac{\int_0^L \delta C(x)\,dx}{L} = C_{max}\int_0^L e^{-\frac{x}{L}}\,d\frac{x}{L} = 0.632 C_{max}. \quad (9)$$

One embodiment of the present invention uses Equation (9) to estimate the maximum concentration $C_{max}$ from the average concentration in the plume.

Combining Equations (5) and (9) gives:

$$C_{max} = -\frac{\left[\frac{1}{2k_{g,on}}\ln\left[\frac{S_{on}}{S_{off}}\right] + C_0 R\right]}{0.632 L}, \quad (10)$$

One embodiment of the present invention evaluates an indication of the presence of the gas of interest from the estimate of the average excess concentration of a gas of interest in a plume, $\overline{\delta C}$, from Equation (10), measurements of $S_{on}$ and $S_{off}$ and estimates or measurements of $k_g$ at the on-wavelength, $C_0$, R, and L.

In alternative embodiments of the present invention, image I includes an image S' of surface S within the mapped scene. It is preferred, though not necessary, that the wavelength of light used to generate image S' is of a wavelength that is not absorbed by the gas of interest G. Thus, for example, the wavelength or wavelengths used to generate image S' may include off-wavelength $\lambda_{off}$ or the wavelength $\lambda_3$ used for determining range R. One embodiment of the present invention, the intensity of backscattered light, $S_\lambda$, for example $S_{\lambda_{off}}$ or $S_{\lambda_3}$, is used to generate image S' according to the scanning of the light beams by system 100.

Alternatively, for embodiments where range R is measured, the intensity of backscattered light, $S_\lambda$, for example $S_{\lambda_{off}}$ or $S_{\lambda_3}$, may be normalized at each pixel of image S' using the measured range R. In general, the intensity of backscattered light decreases with distance from surface S to system 100. Thus, for a given intensity of beam A, the intensity of backscattered light B decreases with R. Images of the backscattered light are thus more intense (brighter) for close surfaces and less intense (dimmer) for surfaces that are more distant. The measured range R, can be used to correct for variations due to this effect. In one embodiment, the decrease of backscattered intensity is approximated as decreasing with the inverse square of the range R. Thus, as one example of this embodiment that is not meant to limit the scope of the present invention, the measured distance R for each pixel within image S' is used to correct the decrease of intensity $S_\lambda$ by calculating $S_\lambda/R^2$ and displaying an indication proportional to $S_\lambda/R^2$ (as a color or shade of grey) at each pixel location, where $S_\lambda$ is, for example, $S_{\lambda_{off}}$ or $S_{\lambda_3}$.

In an another alternative embodiment of the present invention, two off-wavelength measurements are made. Thus, for example, Measurements in Methane The present invention will now be considered in greater detail as being used for the detection of methane leaks in air. In selecting the on- and off-wavelengths, $\lambda_{on}$ and $\lambda_{off}$, the absorption of methane and the other constituents in air should be considered. One choice for $\lambda_{on}$ and $\lambda_{off}$ is illustrated in the absorption spectra 600 of FIG. 6 as the corresponding wavenumber $\overline{v}_{on}$ and $\overline{v}_{off}$. While there are many such wavelengths suitable for making differential absorption measurements, the peak of the R-branch of methane absorption is particularly useful, as it falls outside of absorptions of other atmospheric gases. A strong methane absorption band in the mid-IR is the $v_3$ rovibronic band centered at about 3018 cm$^{-1}$. One particularly useful wavelength is at the R-branch absorption line $\overline{v}_{on}=3057.7$ cm$^{-1}$ ($\lambda=3.2704$ μm). Spectra 600 includes a first curve 601 calculated for a single pass through a methane plume having a density of 10 ppm-m, and a second curve 603 for what is assumed to be the only significant interfering species, water vapor, at a density of 0.038 atm-m, which corresponds to 90% humidity at 90° F. It is evident that this concentration of methane will produce a roundtrip optical depth of 0.11 and will not overlap significantly with water vapor at this high humidity.

Additional inspection of the spectrum of FIG. 6 indicates that $\overline{v}_{on}$ must be close enough to have a lower methane absorption without interference from water vapor. If the laser is centered within +/−1.5 GHz of the peak of the absorption to produce an optical depth within 10% of the peak value. For optimal differential detection, the wavelength $\lambda_{off}$ should be positioned in the valley at the high-wavenumber side of the methane absorption. For optimization of the differential detection within the valley, the wavelength $\lambda_{off}$ should be at least 8 GHz away from the on-wavelength line and positioned at an accuracy of +20/−0 GHz to remain near an absorption minima. In one embodiment of the present invention $\lambda_{off}$ is selected to be from 3269.0 nm to 3269.7 nm, or approximately 3269.3 nm.

The wavelength $\lambda_3$ for making the RTTOF measurement should be selected to be away from absorption features of atmospheric gases, preferably in the eye-safe range of $\geq 1400$ nm.

With one pair of wavelengths for making the differential absorption measurement identified, for example as above, an embodiment of the present invention for determining the maximum concentration of the presence of plumes of methane in air. Using the estimated background concentration of methane in air of $C_0=1.5$ ppm, and the peak absorption coefficient $k_{g,on}$ of 0.005, Equation (5) gives:

$$\overline{\delta CL} = -\left[100\ln\left[\frac{S_{on}}{S_{off}}\right] + 1.5R\right]. \quad (11)$$

with R having units of meters and $\overline{\delta CL}$ having units of ppm-m. One embodiment of the present invention provides an estimation of the presence of methane using Equation (11), measurements of $S_{on}$ and $S_{off}$, and an RTTOF measurement or estimate of R.

Using the plume model used in deriving Equations (7)-(10), an estimate of the extent of a plume of methane from a gas leak into the environment from the estimate L=10 cm is obtained:

$$C_{max} = -\left[1582\ln\left[\frac{S_{on}}{S_{off}}\right] + 23.7R\right], \quad (12)$$

where $C_{max}$ is in units of ppm and L and R are in units of m. One embodiment of the present invention estimates the average concentration of a methane plume in air from Equation (12) and a RTTOF measurement or estimate of R.

Signal to Noise Considerations for Methane Meaurements

The ability of systems and methods of the present invention to detect gases of interest is limited, in part, by the noise inherent in gathering and discriminating backscattered light and in converting the light into useful electrical signals for processing. The following discussion and calculation is not meant to be an exact or exhaustive analysis of the operation of systems of the present invention, including but not limited to system 100, but is meant to provide guidance in the selection of optical components in one embodiment of the present invention. The assumptions made in the following derivation are used to obtain relationships between the various design parameters of a backscatter absorption system for measuring methane in air.

It is useful to relate a maximum concentration to be detected to the amount of light absorbed. The absorption, $\alpha$, is related to the percent absorption of light (% A) through:

$$\alpha = -\ln\left(1 - \frac{\%A}{100}\right) \quad (13)$$

The absorption due to a methane plume in air can be determined from the spectra of FIG. 5. Using the plume model used of Equation (7), for a backscattered measurement, that is for light making two passes through the plume, through methane with a maximum concentration $C_{max}$, the integrated plume concentration is 0.063 $C_{max}$ ppm-m, the percent absorption, % A, of incident light at $\lambda_{on}$ will be approximately 0.063 $C_{max}$ %. For a $C_{max}$ of 1 ppm to be detected at a signal-to-noise ratio of three, which is a typical detection threshold for analytical measurements, the noise-equivalent absorption is 0.063/3=0.021% ($\alpha$=2.1×10$^{-4}$). Using the plume model of Equations (7)-(10), the integrated methane density and intergrated absorption for a signal-to-noise ratio of 3 is presented in Table 1:

| Maximum Plume Methane Concentration, $C_{max}$, (ppm) | Double-Pass Path-integrated methane density, $\overline{\delta CL}$, (ppm-m) (from Equation (11)) | Double-Pass Path integrated Absorption (%A)* |
|---|---|---|
| 1 | 0.063 | 0.021 |
| 2 | 0.126 | 0.042 |
| 4 | 0.252 | 0.084 |
| 6 | 0.378 | 0.126 |
| 10 | 0.630 | 0.210 |

Table 1 presents, for several maximum methane concentrations, the path-integrated methane density using Equation (11), and path integrated absorption required for a signal-to-noise ratio of 3 using Equation (13) for the exponential plume concentration model presented in the derivation of Equation (11). Within the limits of this plume model, Table 1 allows for an comparison of the minimum detectible methane concentration and the sensitivity of the system and may, for example, be used to estimate the minimum integrated absorption measurement required to determine a certain methane concentration. Thus, for example, a system, such as system 100, is estimated to require the measurement of an absorption of 0.021% to be able to determine a maximum methane concentration in a plume, as modeled, of 1 ppm.

Table 1 can also be used to estimate the maximum methane concentration using the plume model. Thus, for example, if $\overline{\delta CL}$ is determined to have a value of 0.063 ppm-m, then, from Table 1, the estimated maximum concentration of methane is 1 ppm.

For a system such as system 100, sensitivity will now be calculated for differential absorption. It will be assumed that laser speckle is the only source of spatially dependent noise, and that the laser pulse energy and receiver attributes can be calculated using the required backscatter return signal-to-noise ratio and a standard lidar equation. The speckle noise depends varies with the signal intensity, the wavelength of the light collected, and the f/# and diameter of the collection optics. The required energy per pulse to overcome detector noise depends on the transmitter and receiver efficiencies, the atmospheric transmission coefficient, the target range, the target reflectivity, the detector efficiency, the collector size and the diameter and f/# of the collection optics. The results of the calculations using typical values is for single shot measurements shown in FIG. 7 as a plot 700 of the noise in CL (for example, $\overline{\delta CL}$), $\sigma_{CL}$, and the noise-equivalent absorption, $\sigma_\alpha$, as a function of the range, or distance R, assuming a laser pulse energy of 5 μJ, and an f#/1 receiver with a diameter of 8.8 cm (the aperture of the pulsed imager), and a 0.5-mm diameter detector. Plot 700 shows the result of single-shot noise under these conditions as a curve 701 of the contribution from electro-optic noise, a curve 703 of a contribution from speckle noise, and a curve 705 of total noise-equivalent value (the sum of the two terms). The speckle term is range independent and is determined by the geometry of the illumination and the collection optics. Speckle limits the single-shot noise floor to a value of about 1.2% absorption. The contribution from electro-optic noise is minor relative to speckle, except at long standoff ranges.

One method of reducing time random noise is by signal averaging. If, for example, more than one set of data is obtained for each pixel of image I, then it is possible to signal average to improve the detection limit. Assuming that it is required to obtain an image in a certain amount of time, a frequency measurement speed, $f_m$, will be required, the effect of the repetition rate of beam A on the minimum detectable concentration of a gas of interest can be calculated in terms of the laser repetition rate $f_1$ as:

$$C_{avg} = C_{os}\left(\frac{f_m}{f_l}\right)^{\frac{1}{2}},$$

where the subscripts refer to data that is averaged ("avg") or that is obtained from one-shot ("os"). This may be applied to the present invention by obtaining multiple measurements over one imaged pixel surface area, for example P(i,j) to increase the sensitivity of the system. Using the results of FIG. 7, and the above equation, the required laser repetition frequency $f_m$ for the scenarios of FIGS. 2 and 3 have been calculated as 77 Hz and 273 Hz, respectively.

If there are sources of noise that are not time random, such as spatially random noise due to laser speckle or temporal variations in the optical characteristics of surface S, then the noise may be reduces by averaging measurements within a surface area corresponding to a pixel. Thus, for example, if 10 measurements can be made within the area of a pixel, for example P(i,j), then this will have the effect of averaging out spatially dependent noise. Alternatively, slight movements can be induced in the position of the laser so that it will illuminate the same area H, but will also produce slightly different speckle patterns.

Because of the finite duration of the mapper sweep, the electronic frequency range over which noise affects the data is limited by setting $S_{on}/S_{off}=1$ at the edges of the scan (i.e. it is assumed that there is no plume at the edges of the scan). Therefore, the frequency cutoff of noise that affects the measurement is approximately:

$$v_{noise} \geq \frac{f_m}{2n}$$

where n is the number of points in a line. For the residential application this equals a frequency of 0.27 Hz, while for the driving application it equals 0.48 Hz. Relative variations of the on- and off-signals at frequencies lower than this should not affect the measurement.

Figure 8:
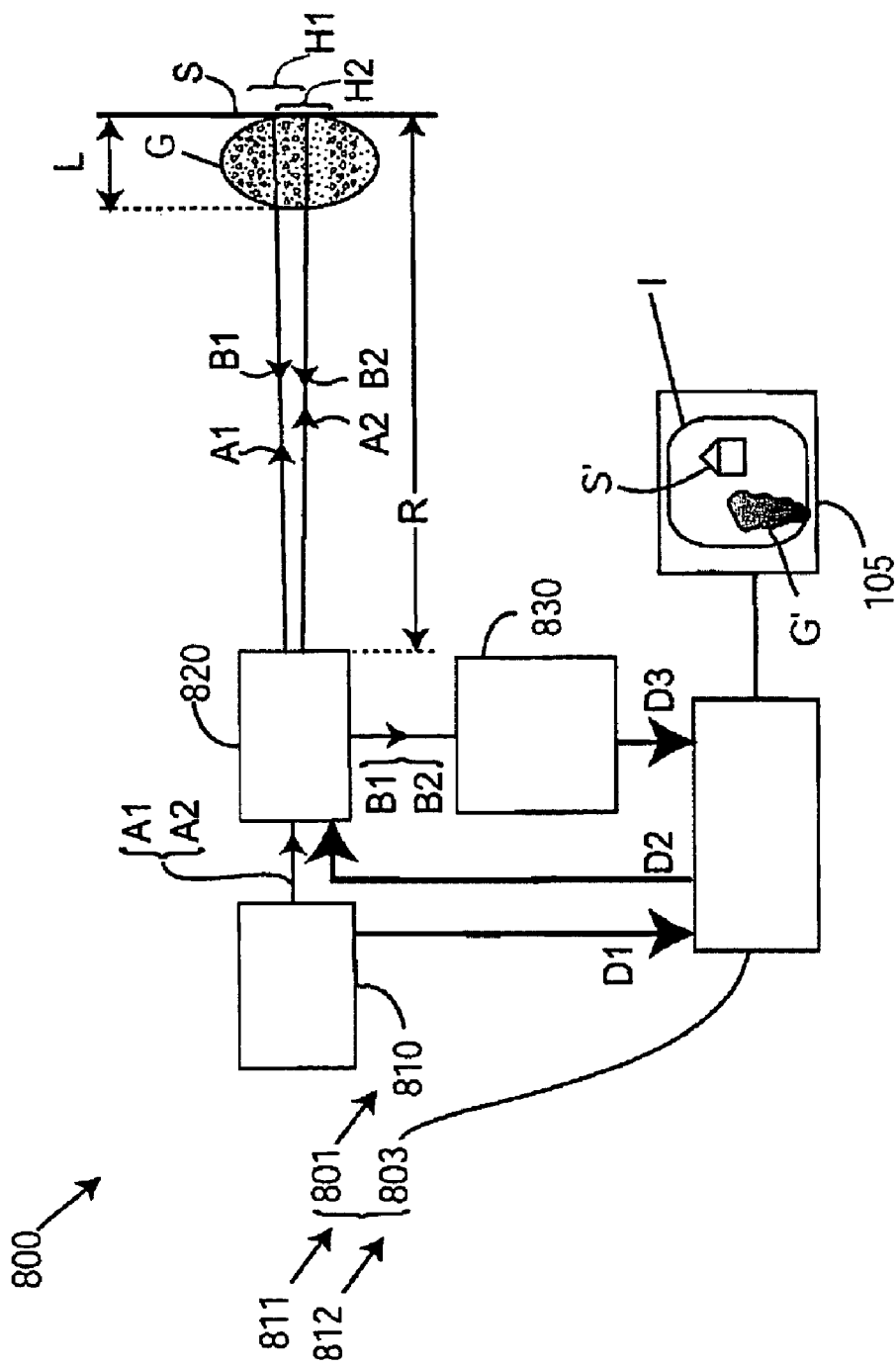
FIG. 8 is another embodiment of the gas mapping system of the present invention.

FIG. 8 depicts another embodiment of gas mapping system 800 for measuring methane in air, which may be generally similar to the embodiments of system 100, as illustrated in FIGS. 1, 2, and 3, except as further detailed below. Where possible, similar elements are identified with identical reference numerals in the depiction of the embodiments of FIGS. 1, 2, and 3.

System 800 is a pulsed point mapper and includes an optical unit 801, a computer processor 803, and a display 105. In one embodiment of the invention, optical unit 801 alternately generates two pulses of light each either different spectral qualities indicated in FIG. 8 as a first beam A1 and a second beam A2. When system 100 is directed at surface S, beams A1 and A2 backscatter from areas H1 and H2 as backscatter beams B1 and B2, respectively. The bracket to the left of the beam labels in FIGS. 8-10 indicate beams are alternately generated. A portion of the light from each of beam A1 and A2 may be used in making one of the two intensity measurements required for a differential absorption measurement and a different portion of each of the beams may be used for making a distance measurement. More specifically, beams A1 and A2 each include two wavelengths of light—beam A1 includes light of wavelength $\lambda_1$ and $\lambda_3$, and beam A2 includes light of wavelength $\lambda_2$ and the common wavelength $\lambda_3$. The alternating wavelengths $\lambda_1$ and $\lambda_2$ correspond to on- and off-wavelengths, respectively, for example $\lambda_{on}$ and $\lambda_{off}$ corresponding to $v_{on}$ and $v_{off}$ for methane in FIG. 6. the for making absorption measurements of the gas of interest, and the common wavelength $\lambda_3$ is used for making the RTTOP measurement. In system 800, the light at wavelengths $\lambda_1$ and $\lambda_2$ is optimized to obtain an accurate signal amplitude, and not necessarily for accurate timing. The wavelength $\lambda_3$ is selected to be at a wavelength of about 1.6 µm, which is both eye-safe and away from absorption features, and for which fast, sensitive, inexpensive detectors are available.

Gas mapping system 800 includes a backscatter absorption gas measurement system 811 and range measurement system 812, which may be generally similar to systems 111 and 112, respectively, except as further detailed below. Backscatter absorption gas measurement system 811 includes the portion of optical unit 801 that generates beams A1 and A2 and that detects backscattered light in beams B1 and B2 at the wavelengths $\lambda_1$ and $\lambda_2$, respectively, and the processing of the measurements at wavelengths $\lambda_1$ and $\lambda_2$ in processor 803. Range measurement system 812 includes the detectors of optical unit 801 that detect backscattered light in beams B1 and B2 at wavelength $\lambda_3$, and the processing of the measurements at wavelength $\lambda_3$ in processor 803.

Optical unit 801 includes a multi-wavelength light source 810, a beam steering unit 820, and a receiver 830. Multi-wavelength light source 810 provides light for performing differential absorption measurements of the gas of interest, which in this embodiment is methane, and measuring the path length of the light performing the differential absorption measurement. The alternating pulsed beams A1 and A2 pass through beani steering unit 820, where the directions of the beams are changed to produce a scanning motion. In general, the scanning proceeds with time, so surface S is illuminated alternately by the scanning beams A1 and A2. Each beam A1 and A2 that interacts with surface S and produces has an associated backscattered beam B1 and B2. The backscattered light beams B1 and B2 contain light from the corresponding beams A1 and A2 that are not absorbed, scattered, or otherwise interfered with on the return path. In addition, beams B1 and B2 may contain other light, such as optical emissions from surface S. Beams B1 and B2 pass into beam steering unit 820 and are diverted to receiver 430, where properties of beams B1 and B2 are measured for wavelengths $\lambda_1$, $\lambda_2$, and $\lambda_3$. Electrical signals along connections D1, D2, and D3 allow timing, positioning and intensity information between processor 803 and multi-wavelength light source 810, beam steering unit 820, and receiver 830, respectively, for generating an image I for viewing on display 105. As shown in FIG. 8, beam A1 illuminates an area H1 and beam A2 illuminates an area H2. Differences between the gas concentration from source 810 to areas H1 and H2, as well as difference in the reflectivities of the surface at areas H1 and H2 may result in errors in the estimate of the presence of a gas of interest. It is preferred that there be little difference in the gases and surface properties encountered by beams A1 and A2.

Figure 9:
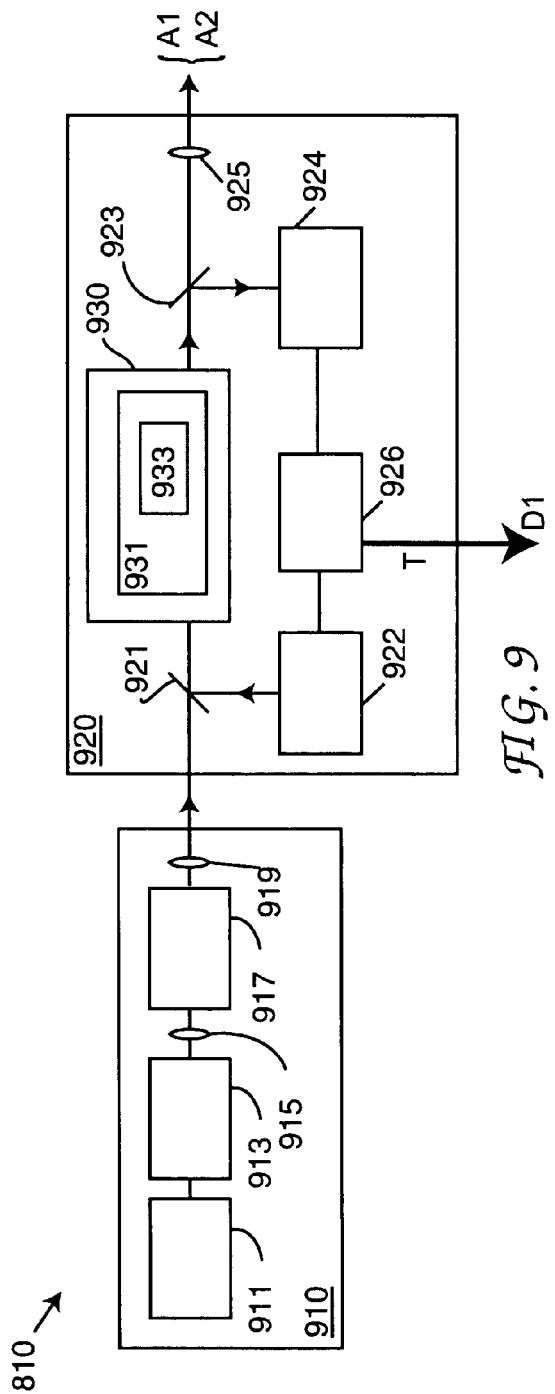
FIG. 9 is a schematic of one embodiment multi-wavelength light source of the present invention.

FIG. 9 is a schematic of one embodiment multi-wavelength light source 810 of the present invention. Source 810 includes a pump laser 910 that generates light at a fixed wavelength and at a repetition rate, and a frequency converter 920 to generate each of the wavelengths used by system 810. In one embodiment pump laser 910 includes a master oscillator 911, an isolator 913, a first lens 915, a power amplifier 917, and a second lens 919. Master oscillator 911 defines the temporal stability, spectral quality, and spatial quality of pump laser 910, power amplifier 917 increases the pulse energy to the required magnitude while preserving the laser beam qualities of master oscillator. Isolator 913 allows light to pass only in one direction—from master oscillator 911 to power amplifier 917. Lenses 915 and 919 are lenses that keep the light focused through light source 810. Alternative embodiments include a fiber laser in place of pump laser 910 and a fiber amplifier in place of power amplifier 917.

In one embodiment of the present invention, master oscillator 911 provides 10 µJ single-longitudinal-mode laser pulses at 1064 nm and a repetition rate of 50 kHz. In one embodiment, master oscillator 911 is a 500-mW active Q-switched laser, such as a CrystaLaser (Reno, Nev.) model QIR1064-500S. Alternatively, master oscillator 911 is a passive Q-switched laser. Isolator 913 protects master oscillator 911 while reducing the CrystaLaser output to 481 mW. Power amplifier 917 is a two-pass Nd:YVO$_4$ amplifier, developed by Aculight (Bothell, Wash.), which amplifies the output to a pulse energy of 111 µJ (5.55 W average power). Power amplifier 917 requires water-cooling, which can be provided, for example, by a BayVoltex (Modesto, Calif.) Mercury MC-0175-AC-19 refrigerated circulator.

A parametric frequency converter 920 accepts the light from pump laser 910 and produces light at two wavelengths which are tunable over a narrow range. OPG modules are described, for example, in U.S. Pat. No. 6,359,914, incorporated herein by reference. Frequency converter 920 accepts the 1064 nm light from pump laser 910 and alternately generates beam A1 of wavelengths frequencies $\lambda_1$ and $\lambda_3$ and beam A2 of wavelengths frequencies $\lambda_2$ and $\lambda_3$. In one embodiment of the present invention, frequency converter 920 is a diode-seeded optical parametric generator (OPG) that includes a beam coupler 921, an OPG module 930, a beam splitter 923, a distributed feedback diode (DFB) seed laser 922, an OPG output diagnostic 924, a frequency controller 926, and a lens 925. DFB diode seed laser 922 is contained in a standard semiconductor package that contains the diode laser, driver, and temperature controller, and that produced continuous output at 1.58 μm. OPG module 930 contains a periodically poled lithium niobate (PPLN) crystal 933 that is 2-5 cm in length, 0.5-1 mm thick, and as narrow as permissible while maintaining structural integrity, for example, from 3-4 mm. Crystal 933 is housed in a thermoelectric-heated oven 931 to regulate its temperature. In one embodiment of the present invention, crystal 993 is a MgO-doped PPLN, which minimizes the heating requirement.

Frequency converter 920 accepts 1.064 μm light from pump laser 910, combines the light in beam coupler 921 with seed laser 922 light at 1.58 μm to pump OPG module 930. Module 930 interacts nonlinearly with the input light to produce light at 3.3 μm. Beam splitter 932 allows light at 1.58 μm and 3.3 μm to pass from frequency converter as beam A1 or A2, while returning the 1.064 μm and a portion of the 1.58 μm and 3.3 μm light to the OPG output diagnostic 924. The exact output frequencies are sensitive to, and are controlled through the seed laser wavelength. Diagnostic 924 includes two photodiodes—one photodiode monitoring transmission through a miniature methane cell and another monitoring the pulse energy. Included with photodiode is signal amplification and sampling electronics.

The exact wavelength of the 3.3 μm light is determined by setting the wavelength of the DFB laser via an adjustment of its drive current or its temperature. The tuning of the 3270.4 nm output relative to the peak absorption of methane is determined by the intensity of the beam transmittance through the miniature methane cell as measured by the photodetector. The monitoring of this transmittance and the adjustment of the diode current to maximize overlap with the methane feature (or to tune off the feature) is accomplished by a digital lock loop operated from the data and signal processor subsystem. The output of frequency converter oscillates between first beam A1 with output 3270.4 and 3269.3 nm, and second beam A2 with output 1577.1 and 1577.4 nm. A timing signal T from frequency controller 926 is used by processor 803 to determine which of the first and second beams A1, A2 are being absorbed and to indicate the beginning of the pulse for the RTTOF measurement.

Figure 10A:
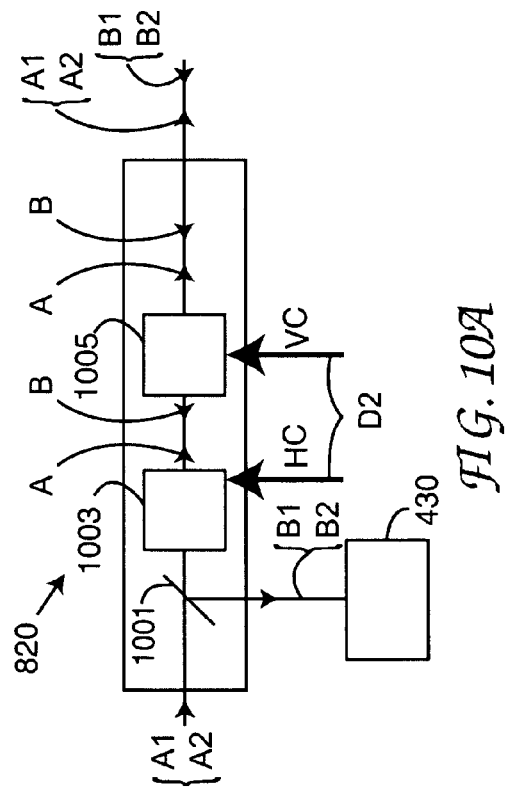
FIGS. 10A-10C are views of one embodiment of the frequency converter of the present invention, where
Figure 10B:
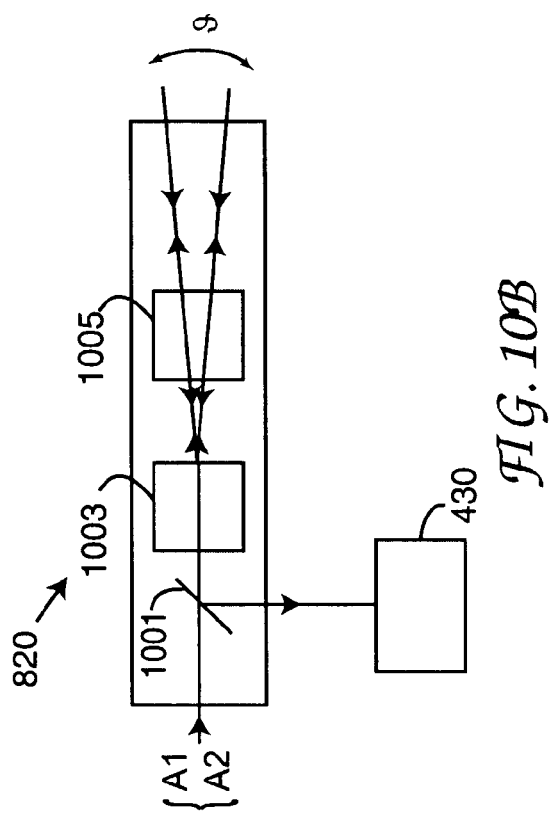
Figure 10C:
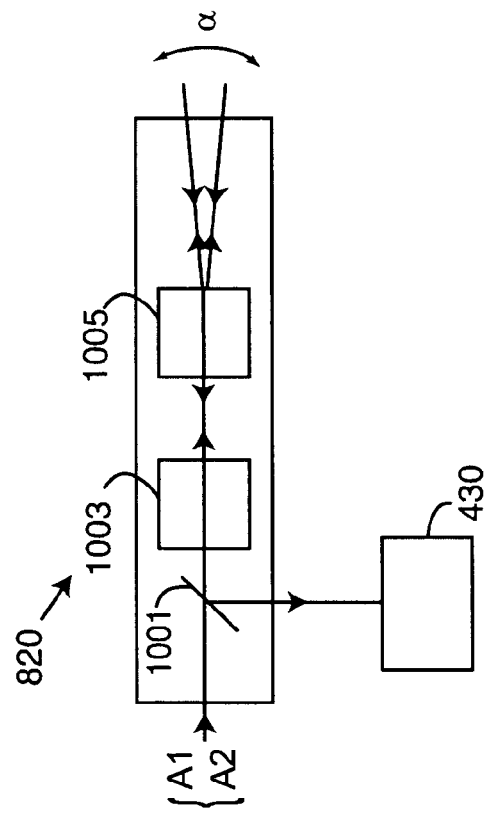

The output of frequency converter 920 is directed as scanning beam by scanner 820, shown schematically in FIG. 10A, and in the top view of FIG. 10B and side view of FIG. 10C. As shown in FIG. 10A, scanner 820 includes a beam splitter 1001, a first mirror 1003 and a second mirror 1005. Beams A1 and A2 alternately pass through beam splitter 1001 and impinging first the first mirror 1003, and then second mirror 1003. First mirror 1003 is a galvometrically driven mirror that rapidly sweeps beam A back and forth in a horizontal plane, through an angle θ, as illustrated in the top view of FIG. 10B Second mirror 1005 is rotated at a slower rate that first mirror 703 in a vertical plane, through an angle α, as illustrated in FIG. 10C. The motion of first and second mirrors 1003 and 1005 is controlled by processor 105 through a horizontal control signal HC and a vertical control signal VC, respectively, that are received from processor 803. The signals HC and VC are controlled to direct beam A to a illuminate a prescribed scan pattern. In the embodiment of FIG. 2, movements of both first mirror 1003 and second mirror 1005 are required to scan an area of a fixed vehicle. In the embodiment of FIG. 3, only movement of first mirror 1003 is required to scan an area of moving vehicle.

Scanner 820 also directs the field-of-view of detectors in receiver 830 along the optical path of beams A1 and A2. Specifically, light from beam A that is backscattered from surface S is directed back through scanner 820 in the reverse direction of beam A. Beams B1 and B2 thus propagate, as shown in FIGS. 10A-10C, off of second mirror 1005 and first mirror 1003. Beam splitter 1001 directs the backscattered light out of the optical path of beam A and towards receiver 830.

Figure 11:
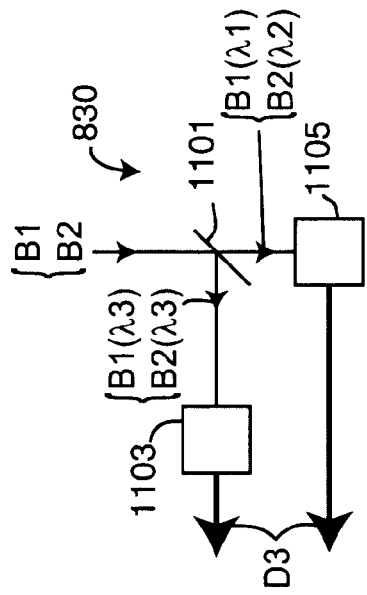
FIG. 11 is a schematic of one embodiment of a receiver of the present invention.

FIG. 11 is a schematic of receiver 830, which accepts beams B, each of which includes light of two wavelengths, and directs the light to one of two detectors. Specifically, receiver 830 includes a beam splitter 1101, a first detector 1103 and a second detector 1105. Beam splitter 1101 preferentially reflects light at $\lambda_3$ towards first detector 1103 and transmits light at $\lambda_1$ and $\lambda_2$ towards second detector 1105. Detectors 1103 and 1105 provide output signals along connection D2 to processor 803.

The output of detector 1105 is proportional to the intensity of beam A at either $\lambda_1$ or $\lambda_2$, for example, $S_{on}$ and $S_{off}$, respectively. This output can be used according to one of the methods described previously to provide a determination of the amount of the gas of interest including, but not limited to, the results of the calculations of Equation (2). In one embodiment of the present invention, which is not meant to limit the scope of the present invention, converter 920 includes a photodetector (not shown) that provides an indication of the intensity of beams A1 and A2 at wavelength $\lambda_1$ and $\lambda_2$ as an intensity $N_{on}$ and $N_{off}$, respectively, which are used to normalize the return beams intensity $S_{on}$ and $S_{off}$ by replacing them by $S_{on}/N_{on}$ and $S_{off}/N_{off}$, respectively, as in Equation (2).

The output of detector 1103 provided to processor 803 is analyzed to determine the RTTOF of the pulsed beam having wavelength $\lambda_3$. In one embodiment of the present invention, which is not meant to limit the scope of the present invention, frequency controller 926 generates a signal for connection D1 indicating the generation of a pulse of light at wavelength $\lambda_3$. The signal from controller 926 and the output of detector 1103 are both provided to processor 803 and are analyzed to determine the time delay between the generation and round trip detection of the portion of beam A having light at wavelength $\lambda_3$, $\Delta t$. The distance from the light source to the backscatter surface, R, is then determined by: $R = c_L/(2 \Delta t)$. The value of R may then be used to provide a correction for the amount of background absorbing gas within the optical path including, but not limited to any one of Equations (11), (12), for example, or by normalizing the values of $S_{on}$ and $S_{off}$ by replacing them by $S_{on}/N_{on}$ and $S_{off}/N_{off}$ respectively.

In one embodiment of the present invention, more than one measurement of backscattered light at each wavelength $\lambda_1$, $\lambda_2$, and $\lambda_3$ is obtained for each area P(i,j), which corresponds to one pixel p(i,j) of image I. Signal averaging can then be performed, for example by averaging an estimate of individual calculations of methane concentration for an area P(i,j), and the resultant signal averaged results can be formatted for display as image I. The results can then be used, for example, to determine a maximum methane concentration using the methods indicated by Equation (11) and Table 1, as described previously.

Signal averaging over the imaged area of individual pixels decorrelates the speckle pattern. In addition, system 800 measures on- and off-wavelength intensities within a sufficiently short time period to ensure that there are no signal variations due to sampling of a different portion of the target surface due to motion of the system field-of-view or laser aiming point between pulses, or due to fluctuations of the target itself.

In alternative embodiments of the present invention, the output of detector 1103 is used to generate an image of light scattered from surface S according to the position of the scanning beams. The intensity of light detected by detector 1103, at wavelength $\lambda_3$, is not absorbed by the gas of interest G, and thus the intensity will depend primarily on the optical characteristics of surface S and the distance R. In one embodiment of the present invention, the output of detector 1103 for each area P(i,j) is used to generate an image S' of surface S, which is then presented at pixel p(i,j). In another embodiment of the present invention, the output of detector 1103 is normalized by the distance R to each area P(i,j) to account for the decrease of intensity with distance. Thus, for example, the output of detector 1103 is divided by $R^2$ to account for the $1/R^2$ decrease of intensity with distance from the scattering surface.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Thus for example, the determination of the distance, as performed by system 112, may be performed for only some of the pixel locations, or at only one point at a pixel location. The devices and methods of the present invention may also be used to measure a background concentration, for example by directing the system to a location known not to have an excess concentration, that may then be used in place of an estimated background methane concentration. In addition, the methods for determining the amount of methane in excess of a background concentration may also be applied to linescanning mappers.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

It will be understood that the steps of methods are performed in one embodiment by an appropriate processor (or processors) of a processing (i.e., computer) system executing instructions (code segments) stored in storage. It will also be understood that the invention is not limited to any particular implementation or programming technique and that the invention may be implemented using any appropriate techniques for implementing the functionality described herein. The invention is not limited to any particular programming language or operating system.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

We claim:

1. An apparatus for providing an indication of the presence of a gas of interest having a background concentration within a scene having a surface, comprising:
   a backscatter absorption gas measurement system to generate a plurality of light pulses to illuminate the surface and determine an indication of absorption by the gas of interest within the scene, wherein the generated light pulses comprise a plurality of beams comprising a first plurality of beams having a first wavelength of light and a second wavelength of light and an alternating second plurality of beams having a first wavelength of light and a third wavelength of light, wherein the first wavelength of light is absorbed by the gas of interest;
   a range measurement system to determine an indication of the distance from said backscatter absorption gas measurement system to the surface illuminated by said backscatter absorption gas measurement system, wherein the distance is determined from the round-trip time-of-flight of light pulses of the first wavelength; and
   a processor to combine the determined indication of absorption and the determined indication of the distance to provide an indication of the presence of the gas of interest in excess of the background concentration, wherein the determined indication of absorption is a differential absorption measurement determined by said processor from said second and third wavelength, and wherein the indication of the presence of the gas of interest includes a presentation of an image of the scene on a display wherein the image comprises a plurality of pixels, wherein each pixel corresponding to a portion of the surface is sufficiently illuminated to perform at least one absorption determination and one distance determination.

2. The apparatus of claim 1, wherein said plurality of beams of light includes light of a first wavelength not absorbed by the gas of interest and wherein said backscatter absorption gas measurement system measures the intensity of backscattered light of said first wavelength, and wherein said processor combines said measured intensity of back scattered light of said first wavelength into an image of the scene, and said presentation further includes the presentation, on said display, of said image of the scene.

3. The apparatus of claim 2, wherein said processor formats said measured intensity and said determined distance into said image of the scene.

4. The apparatus of claim 3, wherein said image of the scene includes said measured intensity divided by the square of said determined distance.

5. The apparatus of claim 1, wherein said gas of interest is methane.

6. The apparatus of claim 1, wherein said backscatter absorption gas measurement system includes an optical parametric frequency converter.

* * * * *